(12) United States Patent  
Bhavaraju et al.

(10) Patent No.: US 12,073,075 B2  
(45) Date of Patent: Aug. 27, 2024

(54) WEARABLE APPARATUS FOR CONTINUOUS BLOOD GLUCOSE MONITORING

(71) Applicant: DexCom, Inc., San Diego, CA (US)

(72) Inventors: Naresh C. Bhavaraju, San Diego, CA (US); Eric Cohen, San Diego, CA (US); Arturo Garcia, Chula Vista, CA (US); Katherine Yerre Koehler, San Diego, CA (US); Michael Robert Mensinger, San Diego, CA (US); Eli Reihman, San Diego, CA (US); Brian Christopher Smith, San Diego, CA (US); Peter Hedlund, San Diego, CA (US); Esteban Cabrera, Jr., San Diego, CA (US)

(73) Assignee: Dexcom, Inc., San Diego, CA (US)

( * ) Notice: Subject to any disclaimer, the term of this patent is extended or adjusted under 35 U.S.C. 154(b) by 387 days.

(21) Appl. No.: 15/931,374

(22) Filed: May 13, 2020

(65) Prior Publication Data

US 2020/0272319 A1  Aug. 27, 2020

Related U.S. Application Data

(63) Continuation of application No. 15/391,366, filed on Dec. 27, 2016, now Pat. No. 10,725,652.

(Continued)

(51) Int. Cl.
*A61B 5/145* (2006.01)
*A61B 5/00* (2006.01)
(Continued)

(52) U.S. Cl.
CPC ........ *G06F 3/04883* (2013.01); *A61B 5/0004* (2013.01); *A61B 5/0022* (2013.01);
(Continued)

(58) Field of Classification Search
CPC ........ G06F 3/0488; G06F 3/01; G06F 3/0481; G06F 3/0482; G06F 1/1684;
(Continued)

(56) References Cited

U.S. PATENT DOCUMENTS 6,983,424 B1   1/2006  Dutta
7,346,203 B2   3/2008  Turek et al.
(Continued)

FOREIGN PATENT DOCUMENTS

WO   WO 2014/011488   1/2014

OTHER PUBLICATIONS

International Preliminary Report on Patentability for Application No. PCT/US2016/068747 mailed on Jul. 12, 2018, 08 pages.

(Continued)

*Primary Examiner* — Eric J Messersmith
(74) *Attorney, Agent, or Firm* — Patterson + Sheridan, LLP

(57) ABSTRACT

A system, a method, and a computer program product for providing wearable continuous blood glucose monitoring. In some embodiments, there is provided a method that includes receiving, at a smartwatch, an alert representative of a glucose state of a host-patient coupled to a glucose sensor; detecting, at the smartwatch, a predetermined action indicative of a request to generate a glance view providing an indication of the glucose state of the host-patient; and presenting, at the smartwatch and in response to the detecting, the glance view providing the indication of the glucose state of the host-patient.

30 Claims, 12 Drawing Sheets

Related U.S. Application Data

(60) Provisional application No. 62/271,843, filed on Dec. 28, 2015.

(51) Int. Cl.

| | | |
|---|---|---|
| *G06F 1/16* | (2006.01) | |
| *G06F 3/04883* | (2022.01) | |
| *G08B 21/04* | (2006.01) | |
| *H04W 4/80* | (2018.01) | |

(52) U.S. Cl.
CPC ...... *A61B 5/14503* (2013.01); *A61B 5/14532* (2013.01); *A61B 5/486* (2013.01); *A61B 5/681* (2013.01); *A61B 5/6898* (2013.01); *A61B 5/742* (2013.01); *A61B 5/7435* (2013.01); *A61B 5/7445* (2013.01); *A61B 5/746* (2013.01); *A61B 5/7475* (2013.01); *G06F 1/163* (2013.01); *G06F 1/1684* (2013.01); *G08B 21/0453* (2013.01); *A61B 5/0024* (2013.01); *A61B 5/7275* (2013.01); *A61B 5/7405* (2013.01); *A61B 5/7455* (2013.01); *A61B 2560/0209* (2013.01); *A61B 2560/0295* (2013.01); *G08B 21/043* (2013.01); *H04W 4/80* (2018.02)

(58) Field of Classification Search
CPC ....... G06F 3/04883; G06F 1/163; A61B 5/00; A61B 5/145; A61B 5/14532; A61B 5/681; A61B 5/7435; A61B 5/7445; A61B 5/746; A61B 5/7475; A61B 5/0022; A61B 5/6898; A61B 5/742; A61B 5/0004; A61B 5/14503; A61B 5/486; A61B 5/0024; A61B 5/7275; A61B 5/7405; A61B 5/7455; A61B 2560/0209; A61B 2560/0295; G08B 21/04; G08B 21/0453; G08B 21/043; H04W 4/80

See application file for complete search history.

(56) References Cited

U.S. PATENT DOCUMENTS

| | | | |
|---|---|---|---|
| 7,716,066 B2 | 5/2010 | Rosow et al. | |
| 7,765,112 B2 | 7/2010 | Brown | |
| 8,000,979 B2 | 8/2011 | Blom | |
| 8,635,086 B2 | 1/2014 | Blom | |
| 8,706,516 B2 | 4/2014 | Warner et al. | |
| 8,925,392 B2 | 1/2015 | Esposito et al. | |
| 9,032,337 B2 * | 5/2015 | Oh | G06F 3/04883 715/863 |
| 9,064,034 B2 | 6/2015 | Javitt et al. | |
| 9,183,720 B2 | 11/2015 | Miladin et al. | |
| 9,854,972 B2 | 1/2018 | Mensinger et al. | |
| 9,943,269 B2 | 4/2018 | Muhsin et al. | |
| 2005/0105788 A1 | 5/2005 | Turek et al. | |
| 2006/0111941 A1 | 5/2006 | Blom | |
| 2007/0194939 A1 | 8/2007 | Alvarez et al. | |
| 2009/0112624 A1 | 4/2009 | Brown | |
| 2011/0144455 A1 | 6/2011 | Young et al. | |
| 2011/0193704 A1 * | 8/2011 | Harper | A61B 5/7445 340/573.1 |
| 2011/0320130 A1 * | 12/2011 | Valdes | G01D 18/00 702/19 |
| 2013/0030826 A1 | 1/2013 | Blom | |
| 2013/0102867 A1 | 4/2013 | Desborough et al. | |
| 2013/0112557 A1 | 5/2013 | Javitt et al. | |
| 2013/0192071 A1 | 8/2013 | Esposito et al. | |
| 2013/0324804 A1 | 12/2013 | McKeown et al. | |
| 2014/0118138 A1 * | 5/2014 | Cobelli | A61B 5/4866 340/539.12 |
| 2014/0121477 A1 | 5/2014 | Jin et al. | |
| 2014/0172442 A1 | 6/2014 | Broderick et al. | |
| 2014/0180595 A1 * | 6/2014 | Brumback | G16H 40/67 702/19 |
| 2014/0187890 A1 * | 7/2014 | Mensinger | A61B 5/145 600/365 |
| 2014/0278552 A1 | 9/2014 | Hold | |
| 2015/0097701 A1 | 4/2015 | Al-Ali et al. | |
| 2015/0141076 A1 * | 5/2015 | Libin | H04W 4/60 455/557 |
| 2015/0164390 A1 | 6/2015 | Larvenz et al. | |
| 2015/0173674 A1 * | 6/2015 | Hayes | G16H 40/67 600/300 |
| 2015/0213224 A1 | 7/2015 | Amarasingham et al. | |
| 2015/0289823 A1 | 10/2015 | Rack-Gomer et al. | |
| 2016/0034696 A1 * | 2/2016 | Jooste | G06F 1/163 726/1 |
| 2016/0042172 A1 * | 2/2016 | Chiplunkar | G06F 3/017 726/19 |
| 2016/0206242 A1 | 7/2016 | Esposito et al. | |
| 2016/0224220 A1 | 8/2016 | Ganguly | |
| 2016/0345830 A1 * | 12/2016 | Raisoni | A61B 5/14503 |
| 2017/0098358 A1 | 4/2017 | Bechtel et al. | |
| 2017/0106052 A1 | 4/2017 | Spat et al. | |
| 2017/0185283 A1 | 6/2017 | Bhavaraju et al. | |
| 2017/0185284 A1 | 6/2017 | Bhavaraju et al. | |
| 2017/0193182 A1 | 7/2017 | Mihai | |
| 2018/0075219 A1 | 3/2018 | Klein et al. | |
| 2018/0360392 A1 | 12/2018 | Stubbs et al. | |

OTHER PUBLICATIONS

Esteves et al., Orbits: Gaze Interaction for Smart Watches using Smooth Pursuit Eye Movements. Proceedings of the 28th Annual ACM Symposium UIST'15, ACM Press, New York, (Nov. 5, 2015), pp. 457-466.

Jameson et al., Data Capture of Transdermal Glucose Monitoring through Computerized Appliance-based Virtual Remote Sensing and Alert Systems. J Med Sys. (2011) 36(4):2193-2201.

European Extended Search Report dated Jun. 3, 2019 for Application No. 16882517.2.

International Search Report and Written Opinion dated May 5, 2017 for Application No. PCT/US2016/68747, filed Dec. 27, 2016.

Examination Report No. 1 from Australian Patent Application No. 2020203210, mailed on Jun. 4, 2021, 4 pages.

* cited by examiner

WEARABLE APPARATUS FOR CONTINUOUS BLOOD GLUCOSE MONITORING

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 15/391,366, filed Dec. 27, 2016, which claims the benefit of U.S. Provisional Application No. 62/271,843, filed Dec. 28, 2015. Each of the aforementioned applications is incorporated by reference herein in its entirety, and each is hereby expressly made a part of this specification.

FIELD

The present disclosure generally relates to continuous glucose monitoring.

BACKGROUND

Diabetes mellitus is a disorder in which the pancreas cannot create sufficient insulin. In a diabetic state, a person suffering from high blood sugar may experience an array of physiological side effects associated with the deterioration of small blood vessels. These side effects may include, for example, kidney failure, skin ulcers, bleeding into the vitreous of the eye, and the like. A hypoglycemic reaction, such as a low blood sugar event, may be induced by an inadvertent overdose of insulin, or after a normal dose of insulin or glucose-lowering agent. In a severe hypoglycemic reaction, there may be a high risk for headache, seizure, loss of consciousness, and coma.

A diabetic person may carry a self-monitoring blood glucose (SMBG) monitor which typically requires the user to prick his or her finger to measure his or her glucose levels. Given the inconvenience associated with traditional finger pricking methods, it is unlikely that a diabetic will take a timely SMBG measurements and, consequently, may be unaware whether his or her blood glucose value is indicative of a dangerous situation.

Consequently, a variety of non-invasive, transdermal (e.g., transcutaneous) and/or implantable electrochemical sensors are being developed for detecting and/or quantifying blood glucose values. These devices generally transmit raw or minimally processed data for subsequent analysis at a remote device. The remote device may have a display that presents information to a user hosting the sensor. In some systems, a patient may check his or her glucose level on a hand held computing device. There are challenges to presenting this information discreetly and reliably.

SUMMARY

Methods and apparatus, including computer program products, are provided for wearable continuous blood glucose monitoring.

In some embodiments, there is provided a method that includes receiving, at a smartwatch, an alert representative of a glucose state of a host-patient coupled to a glucose sensor; detecting, at the smartwatch, a predetermined action indicative of a request to generate a glance view providing an indication of the glucose state of the host-patient; and presenting, at the smartwatch and in response to the detecting, the glance view providing the indication of the glucose state of the host-patient.

In some embodiments, there is provided a method that includes determining a quantity of followers being monitored via a dashboard view presented at a display of the smartwatch, the dashboard view including a plurality of icons corresponding to a plurality of host-patients, each of which having a corresponding glucose state; generating a display including the plurality of icons sized according to the determined quantity of followers; receiving a selection of a sized icon from among the plurality of icons; and displaying additional information regarding the corresponding glucose state of the host-patient corresponding to the selected, sized icon.

In some embodiments, there is provided a method that includes receiving, at a smartwatch, an alert representative of a glucose state of a host-patient coupled to a glucose sensor; presenting, at the smartwatch, a user interface view representative of the glucose state; receiving a request to allow a handoff of the presented user interface view to another device; and presenting, at the other device and in response to the handoff, the user interface view.

In some implementations, there is provided a method of presenting a notification bar in the glance view in response to an alert; detecting a user input to view the notification bar. The user input can be a finger swipe or a manipulation of a physical button. The notification bar can include at least one actionable selection. The actionable selection can display a map, displays a glucose trend chart, acknowledges the alert, or dismisses the alert.

In some implementations, the current subject matter can include one or more of the features disclosed herein including the following optional features. The alert may be received via a low power radio access transceiver at the smartwatch. The low power radio access transceiver may be configured in accordance with at least one of Bluetooth, Bluetooth Low Energy, or NFC. The alert may be received from a receiver wirelessly coupled to the glucose sensor via transmitter sensor electronics. The receiver may include at least one of a smartphone and/or a tablet. The receiver may include a continuos blood glucose application configured to interact with the smartwatch. The alert may be received from a remote server. The detecting of the predetermined action may trigger the smartwatch to replace a home screen and/or a default user interface view with the glance view. The smartwatch may trigger, in response to the detecting, a feedback comprising a haptic indicator, an audio indicator, and/or a visual indicator. The predetermined action may include a selection of a certain icon displayed on the smartwatch. The predetermined action may include a selection of a physical button. The predetermined action may include a detection of a certain wrist movement. The predetermined action may include a detection of a certain eye movement of a wearer of the smartwatch. A swipe pattern may be detected. The detected swipe pattern may be mapped to at least one of a plurality of glance views, each of which is mapped to a different swipe pattern; and the at least one glance view may be presented based on the detected swipe pattern. The glucose state may be mapped to at least one of a plurality of glance views, each of which is mapped to a different glucose state; and the at least one glance view may be presented based on the glucose state. The role of a wearer of the smartwatch may be determined. The role may be mapped to at least one of a plurality of glance views, each of which is mapped to a different role; and the at least one glance view may be presented based on the determined role.

The glance view may be presented based on what the smartwatch is directly coupled to. The glance view may provide, in a single user interface view, a graphical indication of the glucose state including a rate of change of the glucose state. The rate of change may be represented by a quantity of arrows presented via the glance view. The glucose glance view may include a current glucose value. A dashboard may be generated, wherein the dashboard may include a plurality of icons corresponding to a plurality of host-patients, each of which having a corresponding glucose state. At least one of the plurality of icons may be selected in order to obtain additional information regarding the corresponding glucose state. The size of the plurality of icons may be varied based on a quantity of the plurality of icons. An order of presentation for the plurality of icons may be varied based on a severity of the corresponding glucose state. The glance view presented at the smartwatch may be handed off to another device to enable presentation of the glance view at the other device.

It is to be understood that both the foregoing general description and the following detailed description are exemplary and explanatory only and are not restrictive. Further features and/or variations may be provided in addition to those set forth herein. For example, the implementations described herein may be directed to various combinations and subcombinations of the disclosed features and/or combinations and subcombinations of several further features disclosed below in the detailed description.

BRIEF DESCRIPTION OF THE DRAWINGS

The accompanying drawings, which are incorporated herein and constitute a part of this specification, show certain aspects of the subject matter disclosed herein and, together with the description, help explain some of the principles associated with the subject matter disclosed herein. In the drawings.

Figure 1:
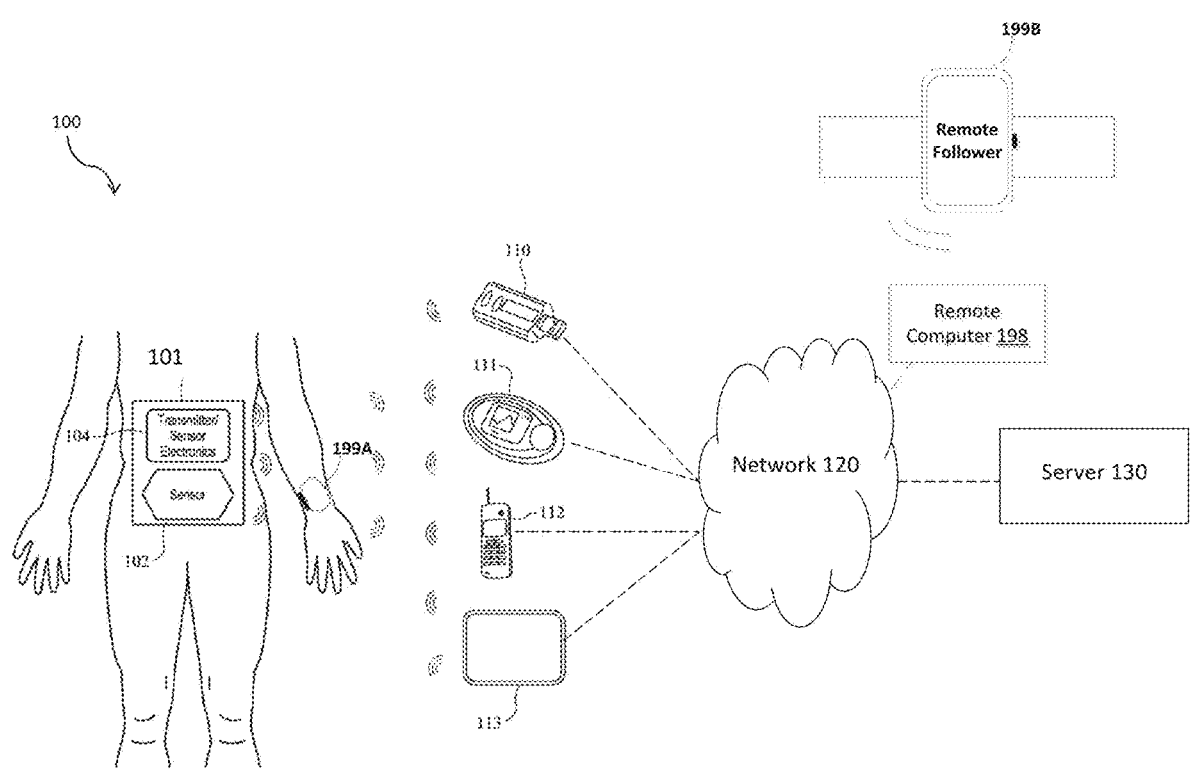
FIG. 1 illustrates a continuous analyte sensor system, in accordance with some example embodiments.

Like labels are used to refer to same or similar items in the drawings.

DETAILED DESCRIPTION

Wearable devices, such as smartwatches, may provide an additional way to provide alerts regarding blood glucose level measurements as well as other types of information and reports to a wearer of the smartwatch. The smartwatch user may be a host-patient being monitored by a continuous blood glucose sensor that wirelessly transmits alerts and other information to a receiver, such as a smartphone, a tablet, a computer, and/or any other device. The smartwatch may receive alerts and other information wirelessly directly from a transmitter associated with the sensor (for example, over a low power radio access technology such as Bluetooth, Bluetooth Low Energy, NFC, etc. or other radio technology including WiFi, cellular, etc.). Alternatively or additionally, the smartwatch may receive alerts and other information wirelessly from the receiver (for example, over a low power radio access technology such as Bluetooth, Bluetooth Low Energy, NFC, etc. or other radio technology including WiFi, cellular, etc.). Alternatively or additionally, the smartwatch may receive alerts and other information wirelessly from any other device, such as a cloud-coupled server.

Although the smartwatch may be beneficial to alerting and monitoring blood glucose and other types of data, the smartwatch may be characterized as having limited display area, when compared to other display devices, such as a smartphone.

In some example embodiments, there may be provide a smartwatch that receives alerts related to blood glucose monitoring, and the alerts and/or reports associated with the alerts may be presented as a user interface view that takes into account the limited display size of the smartwatch.

Before providing additional details for the smartwatch disclosed herein, the following provides an example system description in which the smartwatch disclosed herein may be implemented.

FIG. 1 is a schematic view of a continuous analyte sensor system 100 coupled to a host, such as a patient, and communicating with a number of devices 110-113, in accordance with some example embodiments.

In some example embodiments, a host-patient may wear a sensor assembly 101 as well as smartwatch 199A. The smartwatch may couple wirelessly to a sensor assembly 101 via for example low energy links, such as NFC, Bluetooth, and/or Bluetooth Low Energy, although other radio technologies may be used as well including WiFi and cellular. Alternatively or additionally, smartwatch 199A may couple wirelessly to one or more receivers 110-113 (which may be via low energy links and/or other radio technologies), and the receiver may then couple to the server 130 via the cellular network, the Internet, and/or other types of networks and/or links including wireless links and/or wired links. Alternatively or additionally, smartwatch 199A may couple (via wired and/or wireless links) to server 130. In this way, the smartwatch 199A may receive alerts from the sensor assembly 101, receiver 110-113, and/or server 130.

In some example embodiments, a smartwatch 199B may be worn by someone other than a host-patient. For example, smartwatch 199B may be worn by a remote follower, such as a caregiver, a parent, a teacher, a nurse, and/or any other entity. The remote follower wearing smart watch 199B may receive the same, similar, or different alerts, reports, and/or the like as the host-patient being followed and is wearing smartwatch 199A. Moreover, the remote follower's smartwatch 199B may receive the alerts, other blood glucose information, and/or the like regarding the host-patient from server 130 (via for example the Internet and/or cellular network). Alternatively or additionally, smartwatch 199B may receive the alerts, other blood glucose information, and/or the like from a remote computer 198, smartphone, or other computer-based device coupled to network 120 and/or server 130. When this is the case, the remote computer 198 may use low energy links to communicate with smartwatch 199B. Alternatively or additionally, smartwatch 199B may receive the alerts and other blood glucose information from the host-patient's sensor assembly and/or receive (for example, receiver 112) via for example cellular links and/or other types of wired and/or wireless links.

A transcutaneous analyte sensor system 100 comprising an on-skin sensor assembly 101 is fastened to the skin of a host via a disposable housing (not shown). The system includes a transcutaneous analyte sensor 102 and a transmitter/sensor electronics unit 104 for wirelessly transmitting analyte information to a receiver or CGM receivers, such as devices 110-113. Alternatively or additionally, the sensor may be non-invasive. Alternatively or additionally, analyte sensor 102 and a transmitter/sensor electronics unit 104 may be configured to wirelessly transmit analyte information, such as continuous blood glucose data as well as other types of data being monitored, directly to smartwatch 199A.

During use, a sensing portion of the sensor 102 is under the host's skin, and a contact portion of the sensor 102 is electrically connected to the electronics unit 104. The electronics unit 104 engages a housing (not shown), and the sensor extends through the housing. The housing, which maintains the assembly 101 on the skin and provides for electrical connection of the sensor 102 to sensor electronics provided in the electronics unit 104, is attached to an adhesive patch fastened to the skin of the host.

The on-skin sensor assembly 101 may be attached to the host with an applicator (not shown) adapted to provide convenient and secure application. Such an applicator may also be used for attaching the electronics unit 104 to a housing, inserting the sensor 102 through the host's skin, and/or connecting the sensor 102 to the electronics unit 104. Once the electronics unit 104 is engaged with the housing and the sensor 102 has been inserted and is connected to the electronics unit 104, the applicator detaches from the sensor assembly.

The continuous analyte sensor system 100 includes any sensor configuration that provides an output signal indicative of a concentration of an analyte. The output signal, which may be in the form of, for example, sensor data, such as a raw data stream, filtered data, smoothed data, and/or otherwise transformed sensor data, is sent to a receiver, which is described in more detail below. In various embodiments, the analyte sensor system 100 includes a transcutaneous glucose sensor, a subcutaneous glucose sensor, a continuous refillable subcutaneous glucose sensor, or a continuous intravascular glucose sensor, for example.

In some embodiments, the sensor 102 extends through a housing (not shown), which maintains the sensor on the skin and provides for electrical connection of the sensor-to-sensor electronics, provided in the electronics unit 104. In some embodiments, the sensor 102 is formed from a wire. For example, the sensor can include an elongated conductive body, such as a bare elongated conductive core (e.g., a metal wire) or an elongated conductive core coated with one, two, three, four, five, or more layers of material, each of which may or may not be conductive. The elongated sensor may be long and thin, yet flexible and strong. For example, in some embodiments the smallest dimension of the elongated conductive body is less than about 0.1 inches, 0.075 inches, 0.05 inches, 0.025 inches, 0.01 inches, 0.004 inches, or 0.002 inches. A membrane system may be deposited over at least a portion of electroactive surfaces of the sensor 102 (including a working electrode and optionally a reference electrode) and provides protection of the exposed electrode surface from the biological environment, diffusion resistance (limitation) of the analyte if needed, a catalyst for enabling an enzymatic reaction, limitation or blocking of interferents, and/or hydrophilicity at the electrochemically reactive surfaces of the sensor interface.

The membrane system may include a plurality of domains, for example, an electrode domain, an interference domain, an enzyme domain (for example, including glucose oxidase), and a resistance domain, and can include a high oxygen solubility domain, and/or a bioprotective domain. The membrane system may be deposited on the exposed electroactive surfaces using known thin film techniques (for example, spraying, electro-depositing, dipping, etc.). In some embodiments, one or more domains are deposited by dipping the sensor into a solution and drawing out the sensor at a speed that provides the appropriate domain thickness. However, the membrane system can be disposed over (or deposited on) the electroactive surfaces using any known method.

In the illustrated example embodiment, the electronics unit 104 is releasably attachable to the sensor 102, which together form the on-skin sensor assembly 101. The electronics unit 104 includes electronic circuitry associated with measuring and processing the continuous analyte sensor data, and is configured to perform algorithms associated with processing and calibration of the sensor data. The electronics unit 104 may include hardware, firmware, and/or software that enable measurement of levels of the analyte via a glucose sensor, such as the analyte sensor 102. For example, the electronics unit 104 can include a potentiostat, a power source for providing power to the sensor 102, other components useful for signal processing and data storage, and preferably a telemetry module for one- or two-way data communication between the electronics unit 104 and one or more receivers, repeaters, display devices, such as the devices 110-113, one or more smartphones such as smartphone 199A-B, and/or other devices. Sensor electronics within the electronics unit 104 can be affixed to a printed circuit board (PCB), etc., and can take a variety of forms. For example, the electronics can take the form of an integrated circuit (IC), such as an application-specific integrated circuit (ASIC), a microcontroller, and/or a processor. The electronics unit 104 may include sensor electronics that are configured to process sensor information, such as storing data, analyzing data streams, calibrating analyte sensor data, estimating analyte values, comparing estimated analyte values with time corresponding measured analyte values, analyzing a variation of estimated analyte values, such as estimated glucose values (EGVs), and/or the like.

The devices 110-113 may operate as repeaters, receivers, and/or display devices (also referred to herein more generally as "receivers" or "CGM receivers"). In the example of FIG. 1, device 110 comprises a key fob repeater 110, device 111 comprises a dedicated medical device receiver 111, device 112 comprises a smartphone 112 including an application such as a CGM application to provide the receiver disclosed herein, device 113 comprises a portable or tablet computer 113 including an application such as a CGM application to provide the receiver disclosed herein, although other types of devices capable of receiving, repeating, and/or displaying the CGM sensor data provided by electronics unit 104 may be used as well. Moreover, although the previous example describes the smartphone as including the CGM application, the other devices may include a CGM application as well.

Devices 110-113 may be operatively linked (via wireless link(s), for example) to the electronics unit 104. As noted above, the smartwatch 199A may couple wireless directly to the wireless transceivers at the sensor assembly 101, in which case the smartwatch 199A may be considered a receiver. Alternatively or additionally, the smartwatch 199A may be configured to only couple wirelessly to a receiver 110-113.

The repeaters, receivers, and/or display devices 110-113 may receive data from electronics unit 104, which is also referred to as the transmitter and/or sensor electronics body herein. For example, the sensor data can be transmitted from the sensor electronics unit 104 to one or more of the key fob repeater 110, the medical device receiver 111, the smartphone 112, the portable or tablet computer 113, smartwatch 199A, and the like.

In some implementations, the repeaters, receivers and/or display devices may also transmit data to the electronics unit 104. In some implementations, the repeaters, receivers, and/or display devices may transmit data to one another or to other servers and/or computers. For example, smartphone 111 may receive CGM data from transmitter 104. Smartphone 111 may display the CGM data as well as related alerts and the like. Smartphone 111 may also provide the CGM data to other devices, such devices 110, 112, 113, as well as one or more other servers, such as secure server 130, via for example network 120. In some example embodiments, smartwatch 199A may be configured to transmit information only to a receiver, such as receiver 112. Alternatively or additionally, the smartwatch 199A may be configured to transmit to sensor assembly 101 and/or server 130.

Data output from the output module 101 can provide wired and/or wireless, one- or two-way communication between the receiver and an external computer. This external device can be any device that interfaces or communicates with the receiver. In some embodiments, the external device is a computer or a server, and the receiver is able to download current and/or historical data for retrospective analysis by a patient, a caregiver, a physician, and/or the like for example. In some embodiments, the external device is a modem, and the receiver is able to send alerts, warnings, emergency messages, etc., via telecommunication lines to another party, such as a doctor and/or a family member. In some embodiments, the external device is an insulin pen or insulin pump, and the receiver is able to communicate therapy recommendations, such as an insulin amount and a time to the insulin pen or insulin pump. The external device can include other technology or medical devices, for example pacemakers, implanted analyte sensor patches, other infusion devices, telemetry devices, etc. The receiver may communicate with other devices via any suitable communication technologies and/or protocols including radio frequency (RF), Bluetooth, Bluetooth Low Energy, NFC (near field communications), universal serial bus (USB), any of the wireless local area network (WLAN) communication standards, including the IEEE 802.11, 802.15, 802.20, 802.22 and other 802 communication protocols, ZigBee, wireless (e.g., cellular) telecommunication, paging network communication, magnetic induction, satellite data communication, GPRS, 3G, 4G, 5G, LTE, ANT, and/or a proprietary communication protocol.

The server 130 may have at least one processor and at least one memory storage device that receives, stores, and processes data received from one or more of the key fob repeater 110, the medical device receiver 111, the smartphone 112, the portable tablet computer 113, and other devices including the smartwatches 199A-B. The storage may comprise any type of physical storage, such as RAM, DRAM, SRAM, a hard drive, and/or the like. Moreover, the storage may include a database management system, so that any data can be store in a database in a structured way. A remote device may couple to the server 130 to access sensor data associated with a given host-patient coupled to the sensor/transmitter. For example, a caregiver, a parent, and/or the like at a computer (or smartwatch 199B coupled thereto) may receive, from the server 130 or other device, sensor data, reports, associated alerts, and the like to remotely follow a host-patient at receiver 112. The server may be secure in the sense that a host-patient or other user trying to obtain the host-patient's data may be required to login to the server with a user identifier and a password before accessing sensor data, reports, associated alerts, and the like. Server 130 may also be secure in the sense that patient data may be secured in order to preserve a patient's private data, such as patient identifiable data. The user interface views (for example, a markup language page and/or the like) disclosed herein and/or the information for those views may be generated and/or provided by the server 130, although other devices including a receiver or smartwatch may generate and/or provide the views as well.

The display device, such as a receiver, a smartwatch, and/or any other device, may generate a user interface view for presentation at a display. This display device may include a CGM application configured to generate user interface views including glance views, dashboards, handoff icons, and/or provide other operations including receive, at a smartwatch, an alert representative of a glucose state of a host-patient coupled to a glucose sensor, detect, at the smartwatch, a predetermined action indicative of a request to generate a glance view providing an indication of the glucose state of the host-patient, and present, at the smartwatch and in response to the detecting, the glance view providing the indication of the glucose state of the host-patient. The user interface view may include analyte values, such as CGM data, prompts or messages to convey information to the user, such as reference outlier values, requests for reference analyte values, therapy recommendations, deviation of the measured analyte values from the estimated analyte values, CGM reports (for example, reports including CGM-related information for the host-patient), prompts to guide the user through calibration or troubleshooting of the calibration, and/or the like. A device, such as a smartwatch, receiver, computer, and/or any other device, may download the CGM application, although the CGM application may be provisioned in other ways as well (for example, pre-configured during manufacture and the like).

Figure 2:
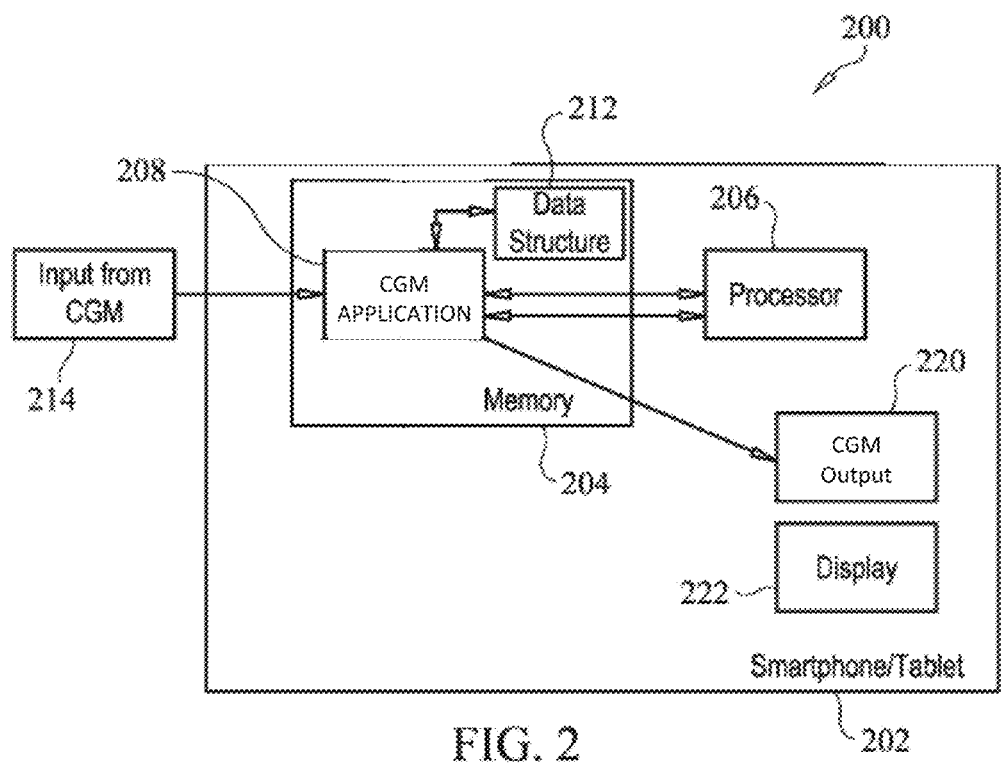
FIG. 2 illustrates a functional block diagram of a mobile device used with the continuous analyte sensor system, in accordance with some example embodiments.

FIG. 2 is a functional block diagram of an embodiment of a system 200 for leveraging mobile device features in continuous glucose monitoring, according to some example embodiments.

The system 200 may comprise a mobile device, which may be any type of computing device capable of receiving one or more inputs and producing an output. Examples of the mobile device include a smartphone 112, a tablet 113 computing device, a laptop, and/or the like. The mobile device 202 may include at least one memory 204 and at least one processor 206. The memory 204 may provide the processor 206 access to data and program information that is stored in the memory 204 at execution time. Typically, the memory 204 may include random access memory (RAM) circuits, read-only memory (ROM), flash memory, etc., or a combination thereof. The processor 206 may be, or may include, one or more programmable general-purpose or special-purpose microprocessors 206, digital signal processors 206 (DSPs), programmable controllers, application specific integrated circuits (ASICs), programmable logic devices (PLDs), etc., or a combination of such hardware-based devices. The mobile device 202 may also include a display, such as a touch sensitive display 222 (also referred to herein as a touchscreen). The mobile device 202 may also include an interface 214 providing CGM data, and an output interface 220 to output data to other devices. In accordance with some embodiments, the processor 206 may execute a continuous glucose monitoring (CGM) application 208 out of the memory 204. In some example embodiments, the smartwatch 199A may be implemented as described with respect to FIG. 2.

In accordance with some embodiments, CGM application 208 may be configured to control, alone or in combination various aspects of the receiver, smartwatch, and/or the like including receive, at a smartwatch, an alert representative of a glucose state of a host-patient coupled to a glucose sensor, detect, at the smartwatch, a predetermined action indicative of a request to generate a glance view providing an indication of the glucose state of the host-patient, present, at the smartwatch and in response to the detection, the glance view providing the indication of the glucose state of the host-patient, provide handoffs, and/or the like. Moreover, the CGM application 208 may be configured to receive data from the transmitter, display CGM data, alerts, messages, and reports (for example, which may be generated by the secure server or generated at the CGM application itself), transmit (or upload) data to other devices, such as server 130, and devices 110-113, and receive data from other devices, such as server 130, and devices 110-113.

In some example embodiments, the CGM application 208 may be downloaded onto the device 200 and comprise a dedicated application, although CGM application 208 may also comprise an internet browser configured to access via network 120 (for example, the Internet) the server 130. The CGM application may also be configured to analyze CGM data provided by a transmitter as well as other data provided by other devices.

As used herein, the phrase "continuous glucose CGM application" should be construed broadly to include not just the application itself, but also integration with sensor 102, other diabetes management devices, including insulin delivery therapies such as insulin pumps, insulin pens, or other drugs useful for the treatment of diabetes. In other words, the CGM application may perform other functions besides monitoring blood glucose. It could, for example, determine that a user's blood glucose level is high, and then transmit a signal to the user's insulin pump to administer a quantity of insulin to bring the user's blood glucose level down.

A software and/or firmware component of the CGM application 208 may be stored in storage 210 available to the mobile device 202, and loaded into the memory 204 at execution time. The storage 210 may be any non-transitory computer readable media including, but not limited to, a hard disk, EEPROM (electrically erasable programmable read only memory), a memory stick, or any other storage device type. The memory 204 may contain one or more data structures 212 that the CGM application 208 accesses during execution. For example, the CGM application 208 may receive an input and store the input as an input parameter in a data structure 212 in the memory 204 for later processing.

In some embodiments, the CGM application 208 may be embodied as downloadable software that a user may download from a remote server, such as server 130, through a wired or wireless connection. For example, the user may access the server 130 using an application already installed on the user's mobile device. The user may then download and install the CGM application 208 with the aid of the application. The user may then configure the CGM application 208. For example, the configuration may include setting the user's personal preferences and/or settings, such as contacts, events, modes, profiles, and/or the like. The configuration may be done manually, such as by selecting various options from menus, or automatically. In automatic configuration, the CGM application 208 reads the user's preferences and/or settings that are stored on the mobile device. The CGM application 208 would first discover what other applications are installed on the mobile device, and then access those applications' data stored in the mobile device's storage and/or remote storage accessible by the mobile device 202 to initially populate the CGM application 208 during set up.

Glance Views

The use of wearable device, such as smartwatches 199A-B and/or the like, may present issues with respect to display size. In the case of a smartwatch for example, the display size may be substantially smaller than other user equipment, such as a smartphone. This small watch display screen may make it difficult to display sufficient information. This small display may also make it more difficult to make a selection via the smartwatch screen. Although some of the examples refer to smartwatches, other type of wearable devices may be used as well.

Figure 3A:
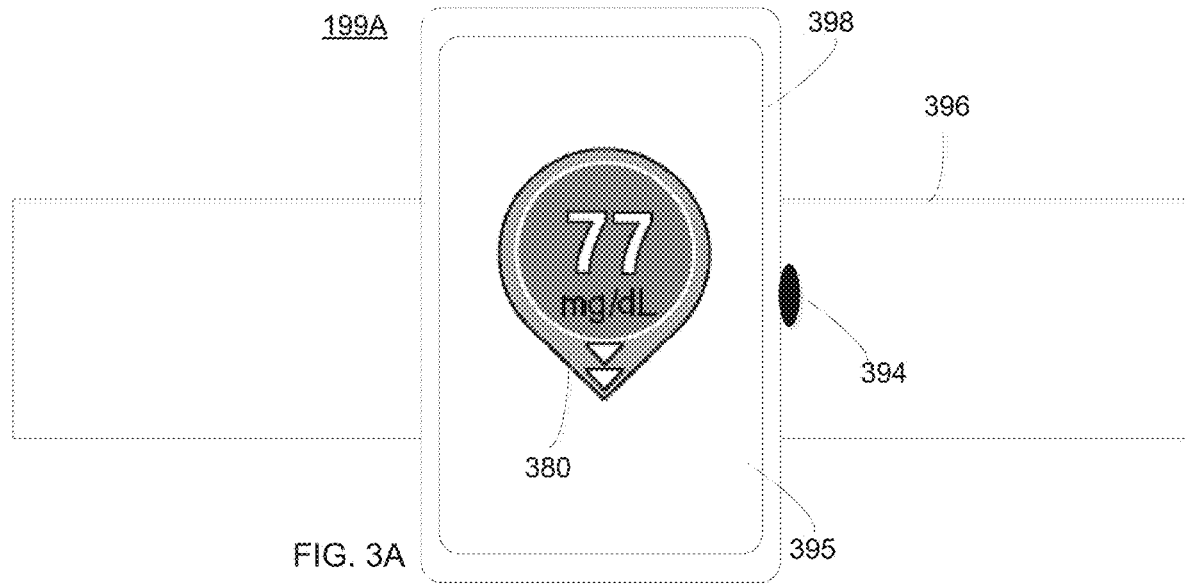
FIG. 3A illustrates an example of a smartwatch including a glance view, in accordance with some example embodiments.

FIG. 3A depicts an example of a smartwatch 199A including a band 396, a case 398, which may include one or more circuits (not shown) such as at least one processor circuit, at least one memory circuit, wireless transceiver(s), and/or other circuitry including touchscreen control circuitry, accelerometer/gyros, power management circuitry, a battery, and/or the like. The smartwatch 199A may also include a display, such as touch sensitive display 395, and include other input-output mechanisms, such as at least one physical button 394 that can be used as an input/output device.

The smartwatch 199A may, as noted above with respect to FIG. 1, include at least one low power transceiver for coupling wirelessly (for example, a Bluetooth transceiver, a Bluetooth Low Energy transceiver, an NFC transceiver, and/or any other low power radio technology transceiver) to a receiver, such as receiver 112, 113, and/or the like, although other higher power radio technologies such as cellular and/or WiFi may be used as well. The receiver, such as receiver 112, may comprise a smartphone that includes a cellular radio transceiver or a WiFi transceiver for coupling to other devices such as other receivers, server 130, and/or any other device, although the receiver may couple to server 130 via wired links as well. The receiver, such as receiver 112, may also include a lower power transceiver, such as a Bluetooth, Bluetooth Low Energy, NFC, and/or the like, for coupling to the smartwatch 199A, as well as other devices including a receiver, such as receiver 112, 113, and/or the like.

Moreover, the receiver, such as receiver 112, may send information, such as alerts to the sensor 102, and the alerts may include a glucose high state of the host-patient coupled to sensor 102, a glucose low state of the host-patient, and/or any other type of alert or information. The alert may be presented at the smartwatch 199A and/or trigger a user interface view, such as a graphical representation of the host-patient's glucose state, an icon, a report, and/or other type of graphical representation.

In some example embodiments, there may be provided a so-called "glance view." For example, a specific gesture on the smartwatch touchscreen 395, such as a swipe up or any other predetermined gesture (which may be configured via smartwatch 199A or via another device such as server 130, receiver 112, and/or remote follower 199B) may trigger presentation of a certain user interface view at the display screen 395 of the smartwatch 199. In the example of FIG. 3A, an alert may be received at the smartwatch 199A. This alert may automatically trigger an indication, such as haptic feedback (for example, vibration), audio feedback, and/or a graphical indication at the display 395. In response, a user may swipe across, which may be a predetermined or pre-configured gesture on the touchscreen display 395. This gesture may be detected by the smartwatch touchscreen circuitry, and trigger the display of user interface view 380. User interface view 380 may provide a so-called glance view because it gives the current glucose level at a glance. In the instant example, the glance view also includes two downward arrows indicate the relative rate that the glucose level is falling. More arrows would indicate a faster fall in the fall in the glucose level, while fewer arrows would indicate a slower rate of descent. A color, such as red, may also be used to indicate the low glucose level is below a threshold level, and a numerical value may also be presented as well.

Although the previous example refers to a gesture such as a swipe on the face of the smartwatch to trigger a certain user interface view such as a glance view, the glance view may be triggered by selection of a certain icon displayed on the smartwatch display 395 screen or a physical button 394 on the smartwatch. In some example embodiments, the glance view may, as noted, be triggered by an accelerometer and/or gyro detecting whether the smartwatch 199A is in view of the wearer's eyes by for example monitoring wrist movement patterns. In some example embodiments, the glance view may be triggered by a camera sensor at the smartwatch 199A detecting the wearer's eyes. Moreover, these events may trigger additional data to be presented. For example, a glance view may be presented on a smartwatch display, but a predetermined type of swipe of other event/action may trigger additional data to be presented, such as more data to be displayed.

Although the previous example describes the glance view being triggered by a gesture, icon selection, or other user-action, the glance view may be presented at the display 395 automatically without the noted triggers.

In some example embodiments, an accelerometer or gyroscope (gyro) in the smartwatch may, as noted, detect patterns in the movement of the arm and/or wrist. The detection may include detecting if a wearer of the smartwatch holds the smartwatch in a certain position (or for a certain time) so that the wearer can view the display of the smartwatch. If so, the smart watch may trigger a glance view or another type of a user interface view without requiring the user to perform a physical selection at the smartwatch.

In some example embodiments, a certain user interface view may be selected by the smartwatch 199A based on a type of alert, such as the state of the host-patient. For example, if the host-patient has a rapidly dropping blood glucose level as in FIG. 3A, a certain user interface view 380 may be presented at the smartwatch display 395. This smartwatch 199A may map the user interface view 385 to the given alert or host-patient state, which in this example is a rapidly dropping blood glucose level. To illustrate further, a rapidly rising blood glucose level alert may map to another user interface view, a fail to acknowledge an alert may map to another user interface view, and so forth.

Moreover, the type of user interface view presented at display 395 may be dynamically selected. For example, as the state of the host-patient changes (as indicated by alerts sent to the smartwatch, for example), the smartwatch 199A may select a certain user interface view based on the host-patient's current state, and as that state changes the alerts and corresponding views presented at the display 395 may change as well. To illustrate, if the host-patient state changes to a high glucose state or a normal glucose state, the smartwatch 199A may select another user interface view to display as the glance view at 395.

In some example embodiments, the certain user interface view presented as a glance view at display 395 may be selected by the smartwatch 199A based on a role of the wearer of the smartwatch. For example, if the wearer of the smartwatch is the host-patient, a user interface view may be presented on the smartwatch 199A display 395 for a high glucose state. On the other hand, if the wearer of the smartwatch 199B is a remote follower, the remote follower's smartwatch 199B may present at display 395 another type of user interface view for a high glucose state. The type of user interface view selected and/or generated based on role of the wearer of the smartwatch may be configured via the receiver 112, smartwatch 199A, server 130, and/or any other device. Moreover, the configured user interface view selected for a given role may be configured by a user, configured as a default, and/or configured or controlled by the server 130.

In some example embodiments, the smartwatch may dynamically zoom to a specific portion of a log or overview report of a plot of glucose measurements.

In some example embodiments, the certain user interface view presented as a glance view at display 395 may be selected by the smartwatch 199A based on how the smartwatch is connected, such as whether the smartwatch is directly coupled to the receiver 112, to the cloud such as cloud-based server 130, and/or to the sensor 102. In some example embodiments, the certain user interface view may be selected by the smartwatch based on the type of connection, such as cellular, WiFi, NFC, Bluetooth, Bluetooth Low Energy, and/or the like.

Figure 3B:
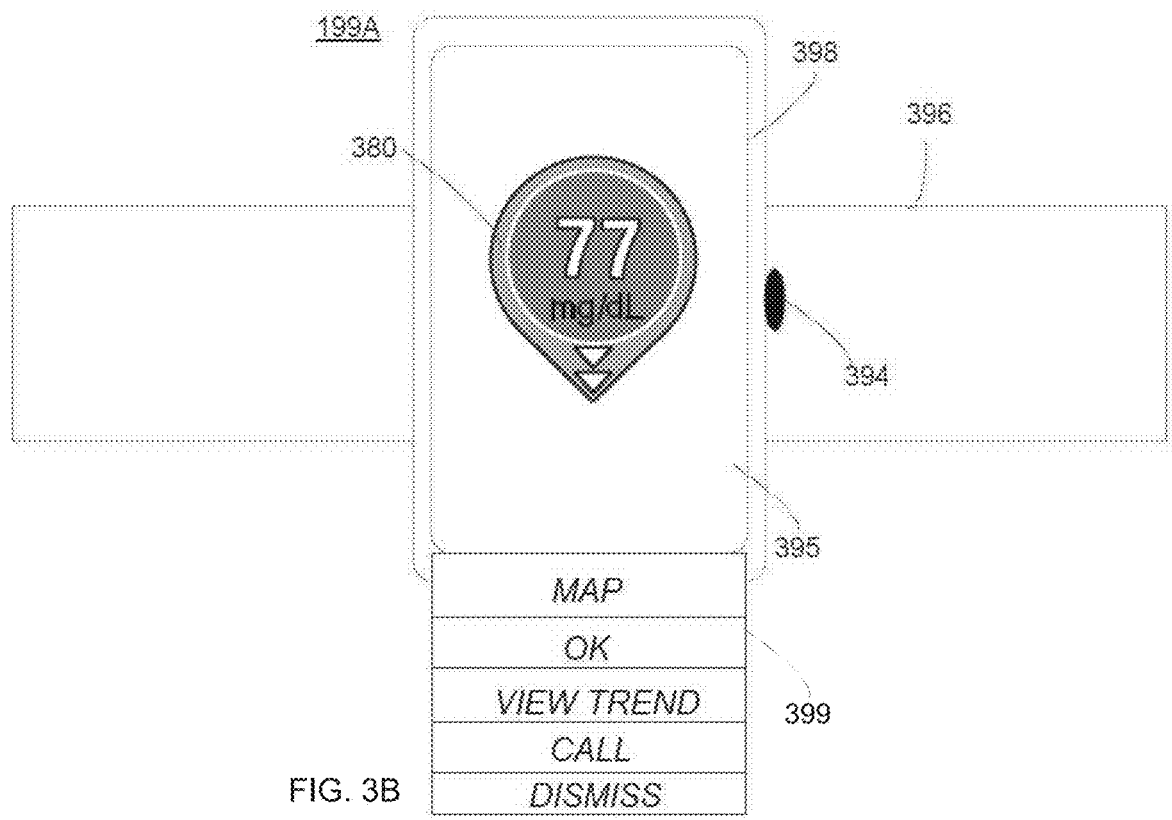
FIG. 3B illustrates an example of a smartwatch including a glance view and notification bar, in accordance with some example embodiments.

FIG. 3B illustrates an example of a smartwatch including a glance view, similar to smartwatch 199A of FIG. 3A, and a notification bar 399. As shown in the figure, notification bar 399 may be located near the lower end of display 395. In other embodiments, notification bar 399 may be located near the upper end of display 395. In some embodiments, notification bar 399 may be hidden from display 395 until a user input is performed. The user input may be performed in response to an alert, as will be discussed below in FIG. 3C. The user input can be a gesture from the user, such as a finger swipe. In some embodiments, the user input can be a rotation or manipulation of button 394. For instance, an upward finger swipe, or a clockwise rotation of button 394, can cause notification bar 399 to scroll upwards. In some embodiments, notification bar 399 may instantaneously scroll or pop up upon detection of an alert without a user input.

The glance view may direct the user's attention to the notification bar 399 upon receiving the alert. For instance, the glance view may display an arrow pointing to notification bar 399, display a glow near notification bar 399, display an animation near notification bar 399, or otherwise highlight the notification bar 399.

In some embodiments, notification bar 399 includes at least one actionable selection. These actionable selections may be hidden in the bottom of the display 395 until the user gestures to scroll the notification bar 399 upwards As the user gestures to scroll notification bar 399 upwards, notification bar 399 may gradually replace the content of display 395 until all of the actionable selections of notification bar 399 are shown. As shown in FIG. 3B, notification bar 399 can include multiple actions for the user to select. These actions can include, for example: show map view, acknowledgement of notification, show trend view, phone call (or text message), and dismiss notification. The map view may display a map that indicates where the host-patient is located. In some embodiments, the map view may indicate where at least one of the followers are located. The trend view may display a glucose trend chart of the host-patient's glucose levels. In some embodiments, the trend view may also display insulin dosage information.

Figure 3C:
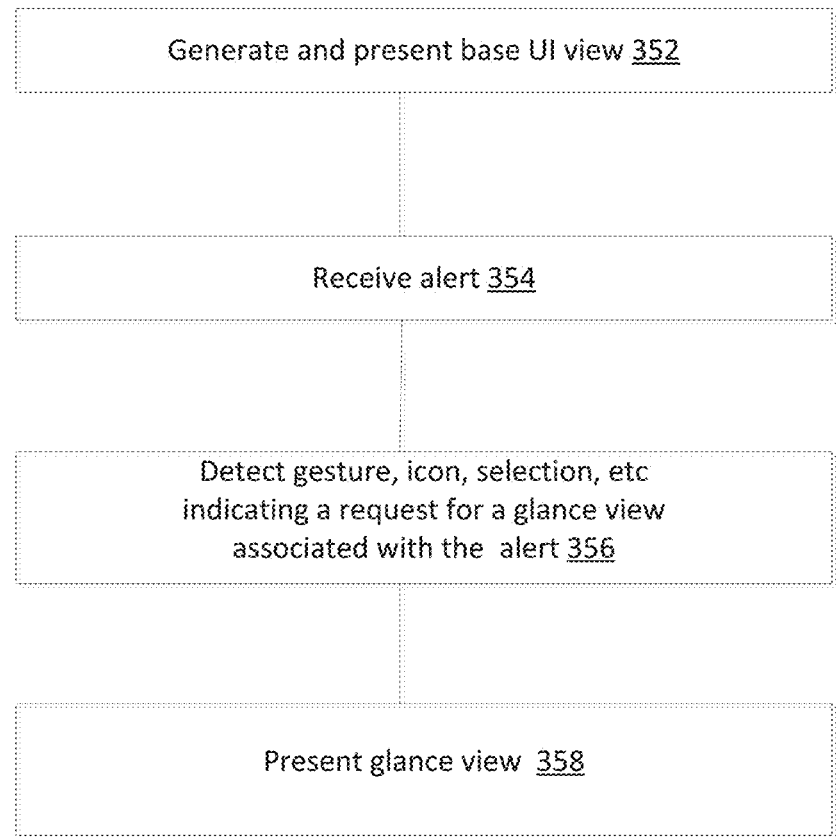
FIG. 3C illustrates an example of a process for triggering the display of a glance view on a smartwatch, in accordance with some example embodiments.

FIG. 3C depicts an example process for generating certain user interface views for a smartwatch, such as smartwatch 199A, in accordance with some example embodiments. The description of FIG. 3C also refers to FIGS. 1 and 3C.

At 352, the smartwatch 199A may generate and present, at display 395, a certain user interface view, such as a home screen or a default user interface view providing certain data related to the receiver 112 or sensor 102, for example. To illustrate, the base view or default view of home screen may include a user interface view that the smartwatch is receiving data from the sensor 102 and/or receiver 112. Alternatively or additionally, the base view or default view may include an indication of the time and/or data.

At 354, the smartwatch 199A may receive an alert. For example, if the host-patient's measured blood glucose level as determined by sensor 102 measures a low blood glucose level and/or a glucose level that is dropping at a certain rate, an alert may be sent to the smartwatch 199A. The alert may be sent from the sensor 102 and/or receiver 112 to the smartwatch 199A via a wireless link, which may comprise a low-power, short-range link (for example, NFC, Bluetooth, Bluetooth Low Energy, and/or the like), although a higher-power, longer range radio technology such as cellular, WiFi, and/or the like may be used as well.

At 356, a glance view corresponding to the received alert may be presented at the display 395 of smartwatch 199A, and this glance view 380 may be presented in response to an event detected at 356. The detected event may comprise receipt of the alert at 354. Alternatively or additionally, the alert may trigger feedback (for example, haptic, audio, and/or visual feedback) to the wearer of smartwatch 199A, and this feedback may prompt the user of the smartwatch 199A to perform a swipe gesture, for example. The event may be detected by touchscreen circuitry at the smartwatch 199A, and then trigger the display of glance view 380. Alternatively or additionally, the glance view 380 may, as noted above, be triggered by selection of a certain icon displayed on the smartwatch display 395, a physical button 394, an accelerometer and/or gyro wrist movement detected patterns, a camera sensor at the smartwatch 199A detecting the wearer's eyes, and/or any other event or action.

At 358, the smartwatch 199A may present the glance view 380. In some example embodiments, the smartwatch 199A may map different types of glance views to different types of swipes. Moreover, certain types of alerts for certain glucose states may be mapped to certain glance views. In addition, the display 395 may include certain icons that when selected via the touchscreen 395 present certain glance views or certain blood glucose data reports. Furthermore, the severity of the glucose state may be mapped to a certain glance view or detailed report. And, the smartwatch 199A may, as noted, map different types of glance views based on the role of the wearer. For example, a remote follower at smartwatch 199B may receive a simple message saying blood glucose level is dangerously low, while the host-patient at smartwatch 199A may receive more detailed information such as glance view 380. In some example embodiments, selecting glance view 380 may trigger a more detailed report to be presented at smartwatch 199A or another device. In addition, the smartwatch may select a certain type of glance view based on what the smartwatch is connected to. For example, if smartwatch 199A is directly coupled to the receiver 112 and/or sensor 102, the smartwatch 199A may present a certain type of glance view, but if the smartwatch 199A is directly coupled to server 130, the smartwatch 199A may be presented another type of glance view.

Dashboards

Figure 4A:
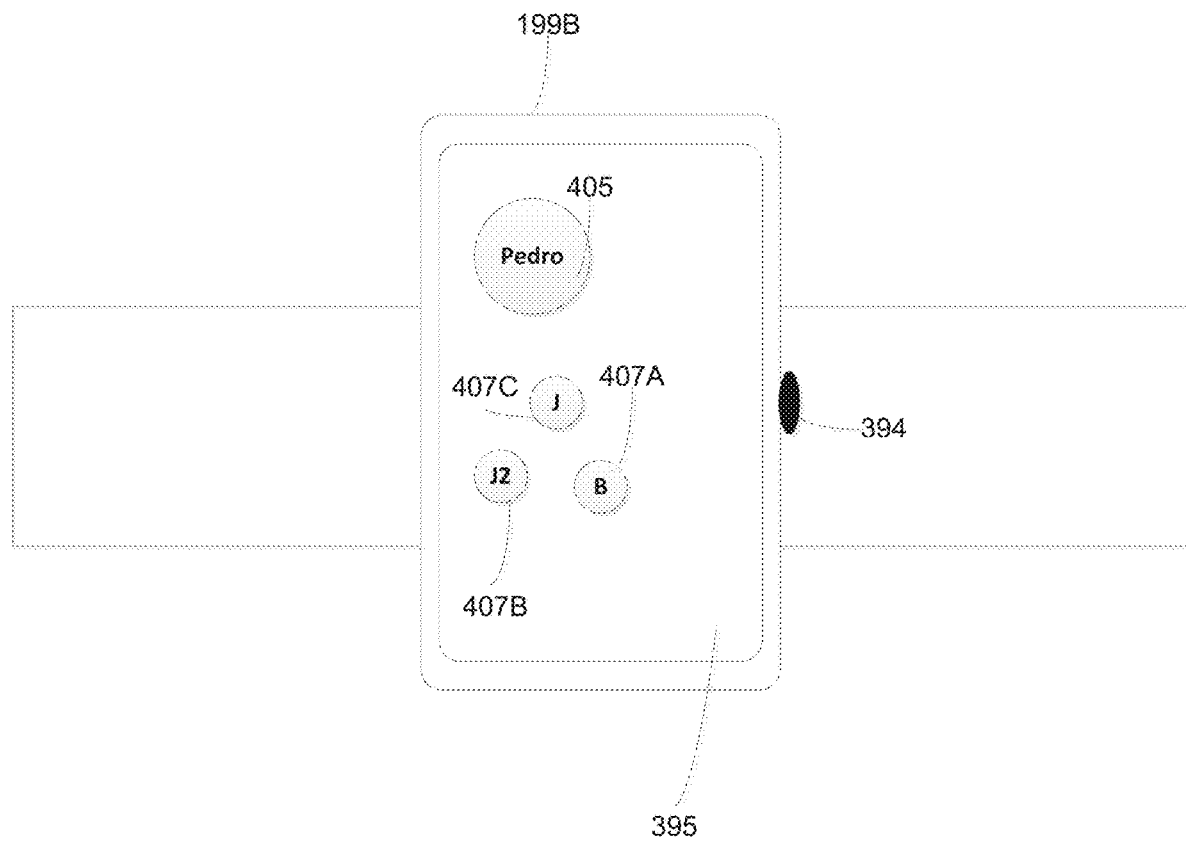
FIGS. 4A-B illustrate examples of smartwatches including dashboards, in accordance with some example embodiments.

FIG. 4A depicts a smartwatch such as smartwatch 199B presenting a dashboard of host-patients, in accordance with some example embodiments. In the example of FIG. 4A, the wearer of the smartwatch 199B may be a so-called remote follower. A remote follower's smartwatch 199B may receive from server 130 information, such as alerts and other information for one or more host-patients, each of which may have a sensor 102 and/or receiver 112, for example.

In the example of FIG. 4A, the dashboard includes icons 405 and 407A-C for 4 host-patients, labeled Pedro, J, J2, and B. In this way, a wearer of the smartwatch 199B may receive alerts, reports, glance views, and/or other information for the 4 host-patients. For example, selecting the icon 405 (labeled Pedro) presented on touchscreen 395 may provide a glance view, an alert, and/or other information including blood glucose information for Pedro. Likewise, selecting the icon 407A (labeled B) presented on touchscreen 395 may provide a glance view, an alert, and/or other information including blood glucose information for Barbara, for example.

Figure 4B:
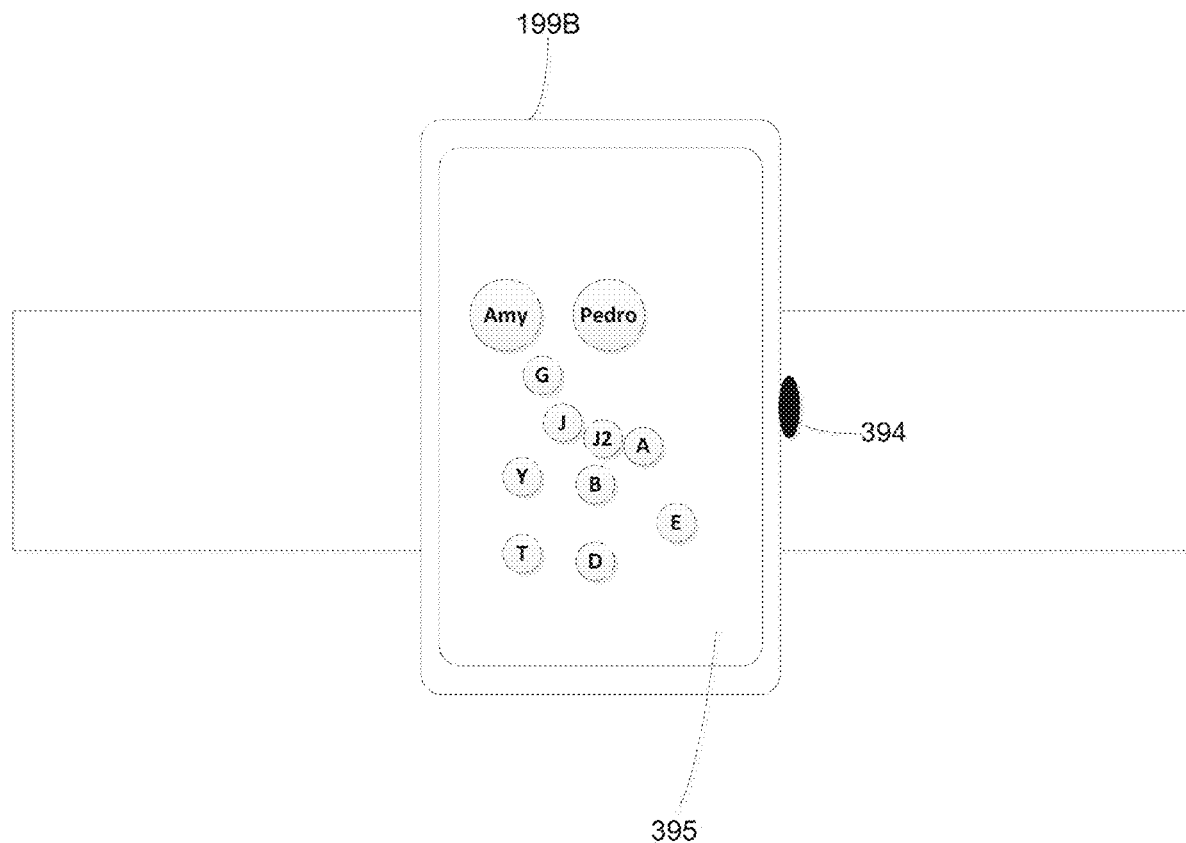

In some example embodiments, the size of the graphical element, such as icon 405, may vary based on the quantity of hosts being followed by the wearer of watch 199B. For example, if the wearer is a remote follower such as a teacher following 4 children, then the icons may have a certain, predetermined size, but if the teacher is following 11 children, then the size of the icon representative of the host-patients being followed by the teacher may be smaller as shown at FIG. 4B.

In some example embodiments, the order of the graphical elements on display 395 may vary based on the severity of the current glucose state of a host-patient. In the example of FIG. 4A, the host-patient represented by dashboard icon 405 may have a more severe glucose state than the other host patients that are located in the lower portion of the screen. Referring again to FIG. 4B, it depicts that the dashboard icons for Amy and Pedro, which are the same size may be more severe than the other icons having smaller size and/or located below Amy and Pedro. For example, Amy and Pedro may have more severe glucose states based on the larger size of the Amy and Pedro icons, when compared to the other icons on display 395 at FIG. 4B for host-patient's, such as G, J, J2, and so forth, which are smaller than Amy and Pedro's icons. In the example of FIG. 4B, the arrangement of Amy and Pedro at the top portion of the dashboard display 395 may also indicate that Amy and Pedro may have more severe glucose, when compared to the other icons on display 395 for host-patient's, such as G, J, J2, and so forth as these other icons are below Amy and Pedro's icons.

Although the previous example used order as the top of the touchscreen display, the order of the icons may be arranged in other ways, such as left to right, right to left, bottom to top, or in any other way to indicate an ordered sequence of glucose severity for the host-patients being monitored via the dashboard. Moreover, the order may be configured by a user of the smartwatch, configured by the server, and/or configured in other ways as well.

Figure 4C:
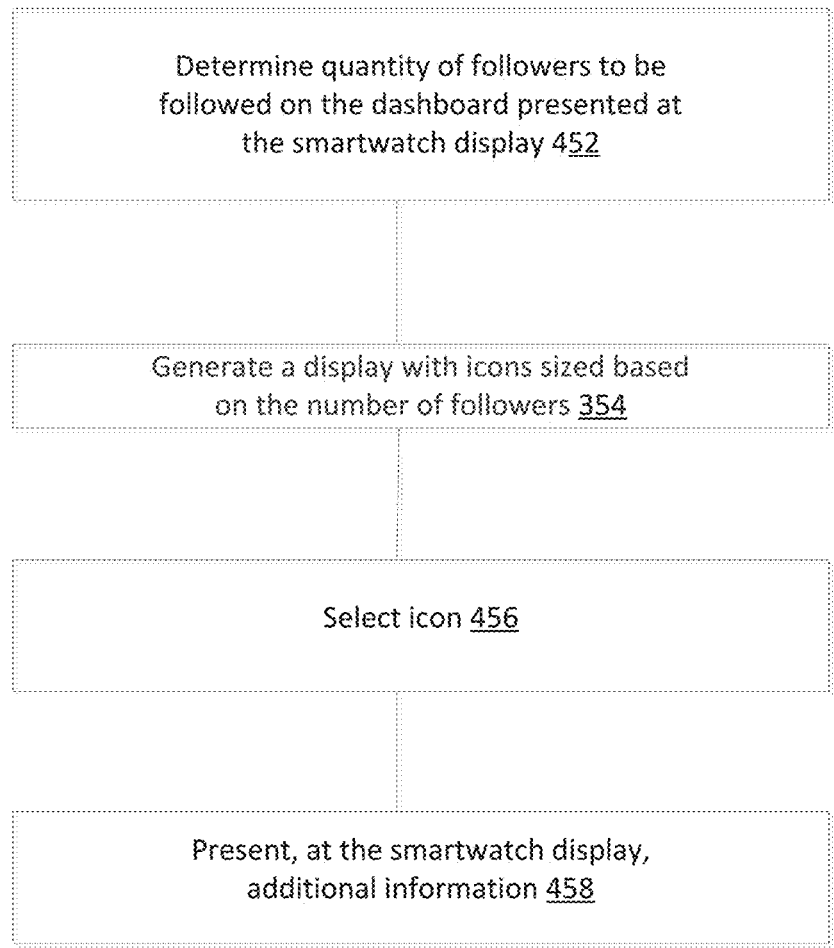
FIG. 4C depicts an example of a process for generating dashboards, in accordance with some example embodiments.

FIG. 4C depicts an example process for generating dynamic dashboards for the smartwatch 199A-B, in accordance with some example embodiments. The description of FIG. 4C also refers to FIGS. 1 and 4A-B.

At 452, the smartwatch, such as smartwatch 199B, may determine a quantity of followers being monitored via a dashboard view at the smartwatch's display 395. The smartwatch may login to server 130, and determine alone or in combination with server 130 the quantity of host-patients (which have a sensor assembly and/or receiver) being monitored. For example, the smartwatch 199B may determine that it is monitoring 4 host-patients (as in the example of FIG. 4A).

At 454, the smartwatch 199B may generate a display with icons sized according to the determined quantity of followers. Based on the determined quantity, the smartwatch 199B may include a size model that configures the size of the icons presented as a dashboard on the smartwatch's touchscreen display. Referring again to FIG. 4A, if the quantity of 4 is determined, then the smartwatch 199B may configure the size of the icons to be a first size, such as the size shown at FIG. 4A, but if the quantity of 11 is determined, then the smartwatch 199B may configures the size of the icons to be another size, such as the size shown at FIG. 4B. Although the previous example refers to specific quantities, the dashboard may display other quantity of icons and size the icons accordingly.

At 456, an icon on dashboard may be selected via the touchscreen 395 or via button 394, and this selection may, at 458, result in additional information, such as a glance view, detailed report, or other information for the selected icon. Referring to FIG. 4A for example, a selection of the icon 405 may be detected by touchscreen control circuitry, and this touch may trigger the display of a user interface view for that patient. Alternatively or additionally, button 394 may be rotated and manipulated to move and select a given icon, such as icon 405.

In some example embodiments, the user interface view may be anonymized by using a code or other representation of the host-patient, rather than a host-patient's name. Referring again to the example at FIG. 4B, Pedro may correspond to number P1, while Amy may correspond to A2. Alternatively or additionally, patient identifying information may not be displayed at the smartwatch. Referring again to FIG. 3A, the glucose state of the host-patient may be displayed at 395 as a glance view 380, but the information may be presented without information identifying the host-patient, such as name of the host-patient, serial number of the sensor or receiver, and/or any other of patient identifying information.

Referring again to FIG. 4A, the color of icon 405 may vary with the severity of the host-patient's glucose state. Alternatively or additionally, audio feedback associated with icon 405's touchscreen selection may vary with the severity of the host-patient's glucose state. Alternatively or additionally, haptic feedback associated with icon 405's touchscreen selection may vary with the severity of the host-patient's glucose state. Alternatively or additionally, icon 405 may vary in some other graphically, audio, or haptically distinctive way based on the severity of the host-patient's glucose state.

Handoffs

Figure 5A:
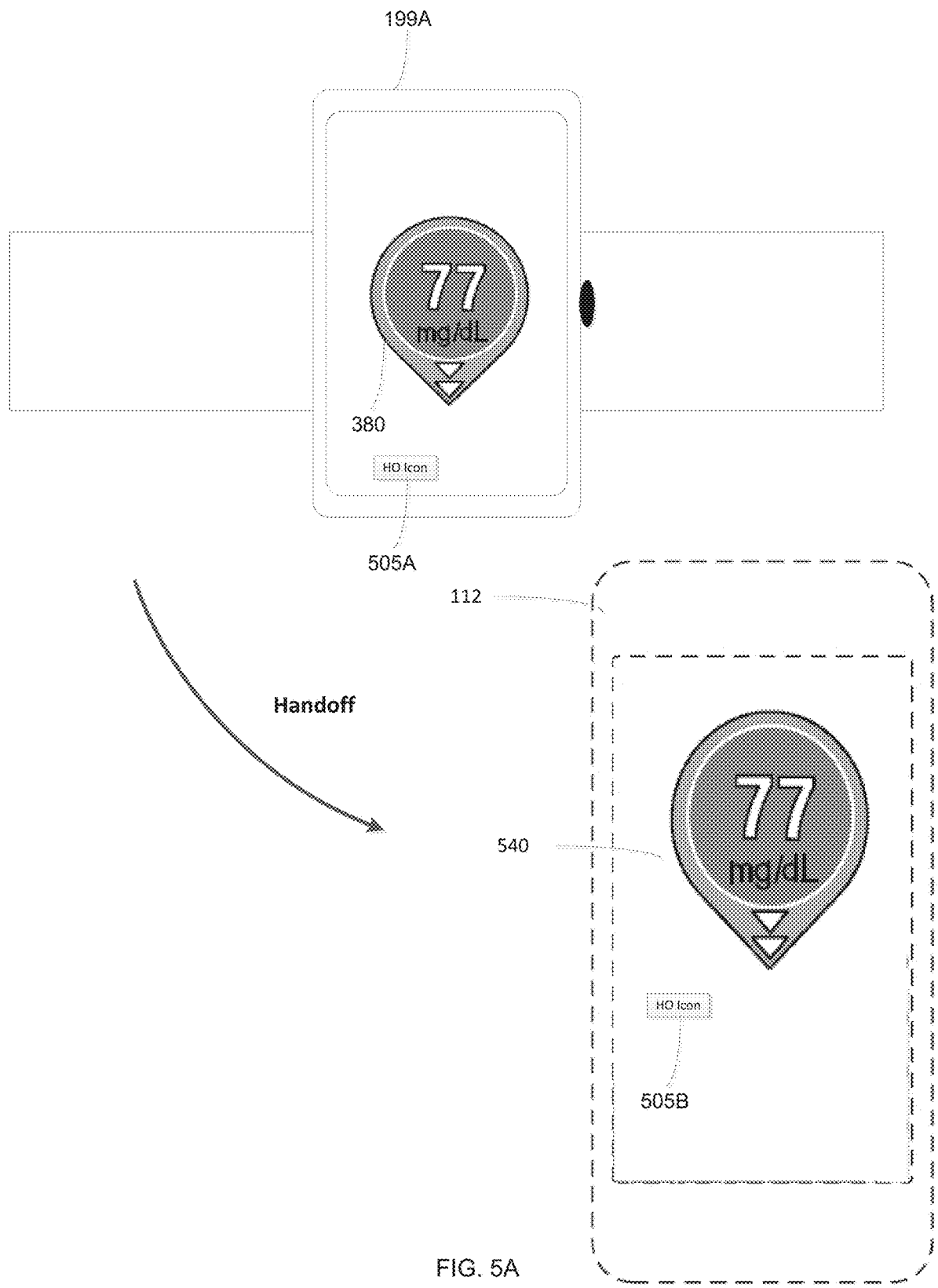
FIGS. 5A-B illustrate examples of smartwatches configured to handoff a display, in accordance with some example embodiments.

FIG. 5A depicts smartwatch 199A presenting a user interface view 380 of host-patient's blood glucose level, in accordance with some example embodiments. In the example of FIG. 5A, the wearer of the smartwatch may enable smartwatch 199A and/or other locally connected devices, such as devices connected via Bluetooth, WiFi, and/or the like, to allow handoffs from the smartwatch 199A to another device. If the user of the smartwatch 199A allows (for example, is configured to provide and enables the handoff) the handoff, the user may move to another device, such as receiver 112, and view the same user interface view 540.

In some example embodiments, the handoff may be enabled by selecting a handoff icon 505A and/or B on the smartwatch 199A and/or receiver 112. When the handoff icon is selected 505, this allows the wearer to view at another of the host-patient's devices, such as receiver 112, the user interface view presented on the smartwatch 199A. For example, smartwatch 199A may be wirelessly coupled via Bluetooth, Bluetooth Low Energy, WiFi, and/or cellular links to receiver 112. Moreover, both devices 199A and receiver 112 may be logged in to server 130 and, in particular, the host-patient's account including blood glucose data and other types of data for the patient. In this example selection of the handoff icon 505A allows the host patient to view the user interface view 380 on another device, such as receiver 112.

In some example embodiments, selection of handoff icon 505A may send a message to the other device. This message may comprise an index or indicator of what is being viewed currently at the smartwatch 199A. When the other device such as smartphone 112 receives this message, the smartphone 112 can determine what was being viewed. Although some of the examples refer to handoff messages being exchanged directly between the locally connected devices, the handoff message(s) may be sent to server 130 as well to assist in the coordination of the handoff between devices, and display the proper content currently being viewed.

Figure 5B:
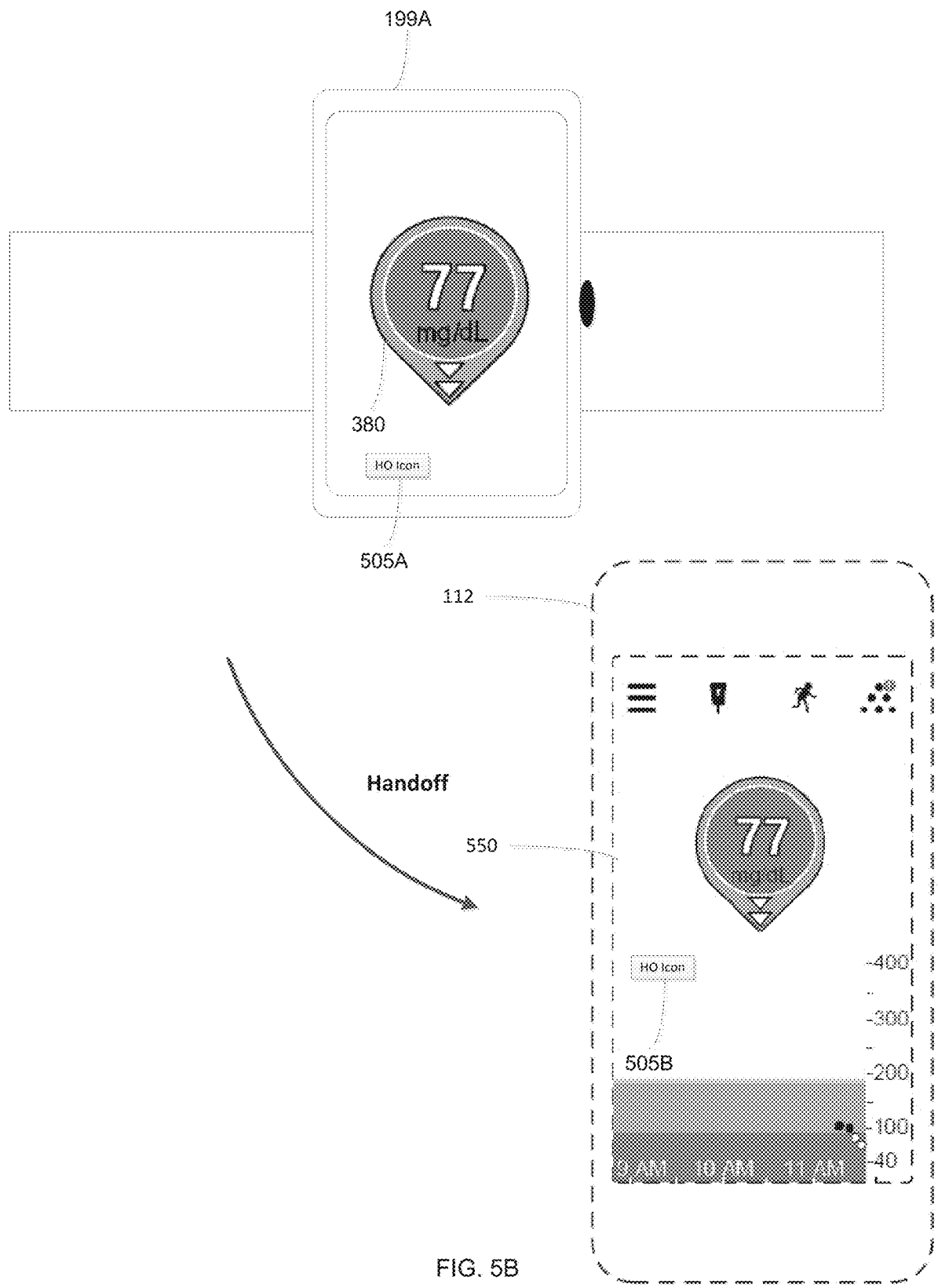

In some example embodiments, selection of handoff icon 505A may trigger another type of user interface view that takes into account the display size on the other device. Referring to FIG. 5B, the handoff is to receiver 112. During the handoff, the smartwatch 199A and receiver 112 may exchange messages, as noted, wirelessly to coordinate the handoff. Next, the receiver 112 may present user interface view 550 that includes, due to the larger display area, additional information when compared to user interface view 380. The type of user interface view presented at the receiver may be selected by the smartwatch 199A, receiver 112, and/or server 130. For example, if a user is viewing user interface view 380 and selects a handoff, when the receiver 112 detects that the user seeks to resume viewing under a handoff condition, receiver 112 may send a message including an index to smartwatch 112 (and/or server 130). This index may indicate what user interface view to present at the receiver 112.

Figure 5C:
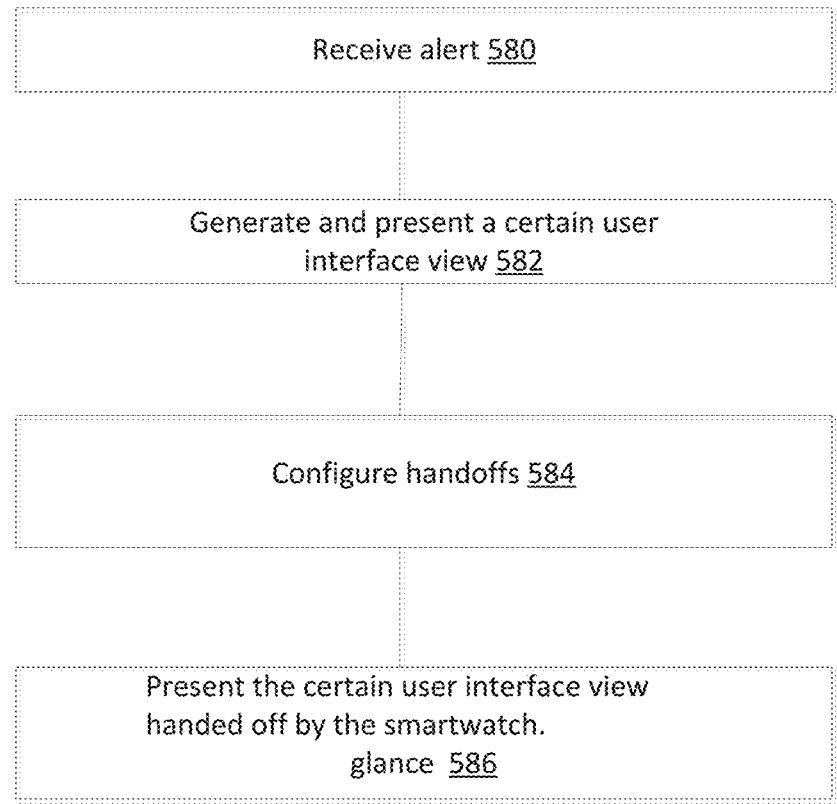
FIG. 5C depicts an example of a process for providing handoffs, in accordance with some example embodiments

FIG. 5C depicts an example process for handoffs among devices, such as smartwatch 199A and smartphone 112, in accordance with some example embodiments. The description of FIG. 5C also refers to FIGS. 1 and 5A-B.

At 580, the smartwatch 199A may receive an alert. For example, smartwatch 199A may receive an alert from the sensor electronics 104 and/or receiver 112, although the alert may be received from other receivers, devices, and/or server 130 as well. In response to the received alert, the smartwatch 199A may generate and present, at 582, a certain user interface view, such as a glance view 380 or a more detailed view, such as a historical log of glucose levels over time. If the smartwatch 199A and other device such as smartphone 112 have configured, at 584, handoffs among devices and allow the handoffs, the smartwatch 199A may send to the target device (which in this example is smartphone 112 to which the user is moving to for access), a message indicating the content that is currently being viewed at smartphone 199A. In some example embodiments, the message may comprise an index pointing to the content being viewed on the smartwatch 199A that the user would like to view at the smartphone 112. In some example embodiments, the server 130 may assist by serving content to the smartphone 112 based on the message or index. In the example of FIG. 5A, the message or index may identify the user interface view 380. To illustrate further, server 130 may have a table listing an index value mapped to user interface view 380. As such, when the user hands off from smartwatch 199A to smartphone 112, the smartphone may request the content from the server 130 based on the index (or from the smartwatch 199A directly without querying the sever 130).

At 586, the other device, such as smartphone 112, may present the certain user interface view handed off by the smartwatch. Referring to the previous example, the smartphone 112 may receive the content (from server 130 and/or smartwatch 199A) and present the handed off content, such as user interface view 380, at the smartphone 112.

Although the handoff may provide the same content, the content handed off to another device may be different. In some example embodiments, the target device receiving the handed off content (such as smartphone 112 in the previous example) may present a user interface view that may be different when compared to what is presented at smartwatch 199A. The target device smartphone 112 and/or server 130) may determine that another user interface view is more appropriate based on screen size (as noted), as well as other factors, such as role of wearer of the smartwatch 112, role of target device user (for example, a remote follower may be presented a different view), severity of alert, a type of gesture on the touchscreen, receipt of a certain type of alert, user preferences, and/or other factors.

Although the previous example describes the handoff to the target device being triggered by selection of a handoff icon, the handoff may be performed automatically without the icon selection. For example, the smartwatch 119 may be configured to handoff to other devices that the wearer of the device is logged into (as well as logged into server 130).

Figure 6:
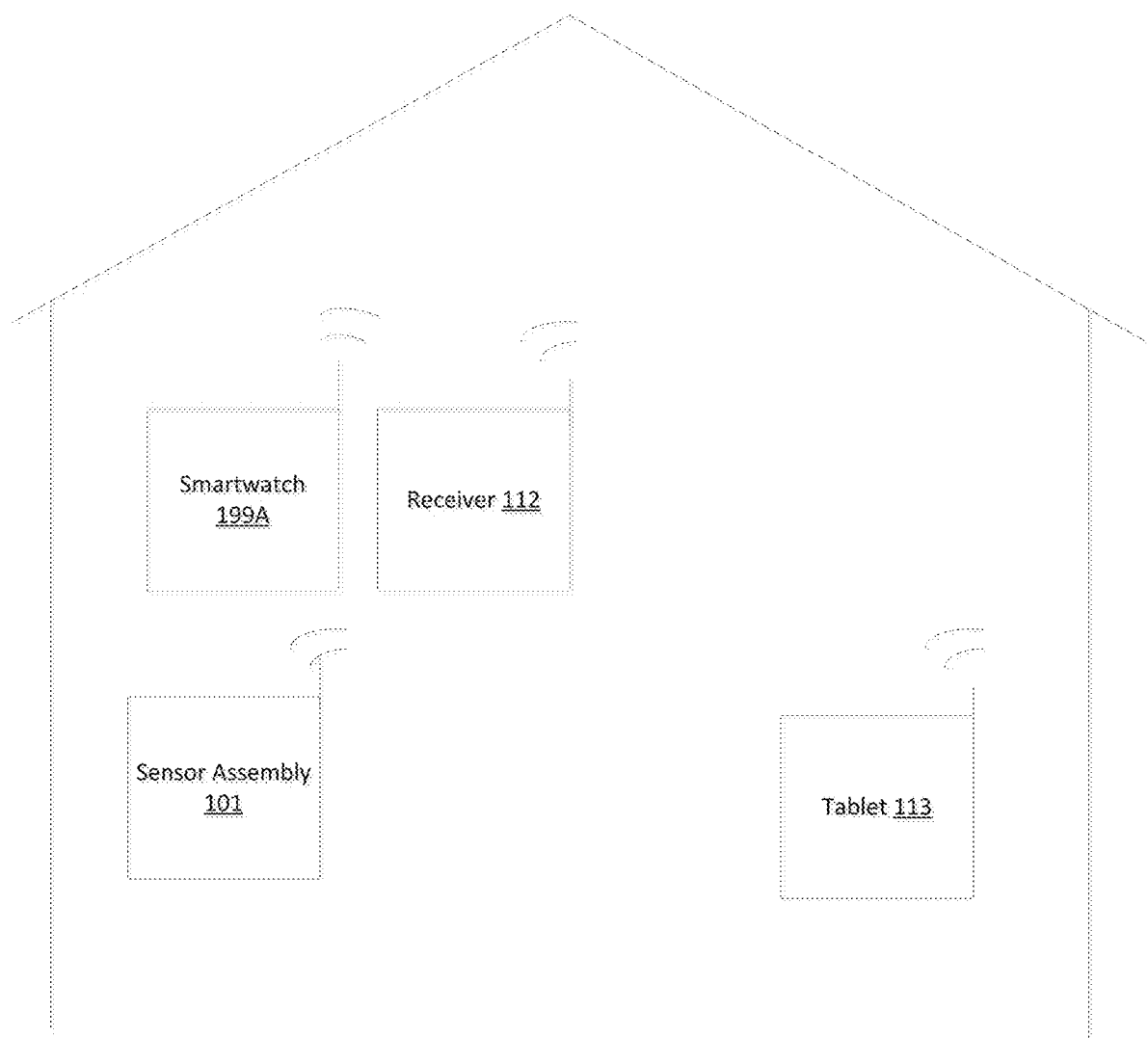
FIG. 6 depicts an example of devices locally coupled, in accordance with some example embodiments.

FIG. 6 depicts an example of a plurality of devices, which may all be associated with the same host-patient. For example, the host-patient may be being monitored by sensor assembly 101, which is wirelessly coupled to receiver 112. Moreover, the host-patient may be wearing smartwatch 199A, and the host-patient may be using a tablet 113 or other type of computer. These devices 101, 112, 199A, and 113 may all be locally connected via local links, such as NFC links, WiFi links, Bluetooth, Bluetooth Low Energy, and/or the like. For example, the devices 101, 112, 199A, and 113 may all be located within the host-patient's home. Moreover, at each of the devices 101, 112, 199A, and 113, the host-patient may be logged in his or her account at server 130 via network 120 (for example, the internet, a cellular network, and/or other networks), so the host-patient is authenticated and authorized to receive his or her alerts, blood glucose data, reports, and/or any other information.

In some example embodiments, a master-slave scheme is provided to prioritize to what device 101, 112, 199A, and 113 an alert or user interface view is generated and presented.

In some example embodiments, each device 101, 112, 199A, and 113 may detect whether it is currently being used by the host-patient, and the device currently being used may signal the others that any alerts, reports, views, should be provided or sent to the device currently being used. If the alert and/or the like is not acknowledge by a host-patient (for example, an icon selection on the display screen to acknowledge), the device currently being used may allow the other devices to generate and/or present alerts, reports, or views.

In some example embodiments, a user may specify a default order indicating what device 101, 112, 199A, and 113 should first present an alert, view, and/or report. If the alert and/or the like is not acknowledge by a host-patient (for example, an icon selection on the display screen to acknowledge), the default order may specify which of the other devices should then present the alert.

In some example embodiments, the state of the host-patient may drive which device 101, 112, 199A, and 113 should first present an alarm, view, and/or report. For example, the order may include alerting a smartphone 112 or a remote follower's receiver or smartwatch.

In some example embodiments, the role of the user may drive which device 101, 112, 199A, and 113 should first present an alarm, view, and/or report. For example, the order may include alerting a remote follower's receiver or smartwatch.

In some example embodiments, the state of the device, such as available power, available connectivity, device health, and/or the like, may drive which device 101, 112, 199A, and 113 should first present an alarm, view, and/or report. For example, a device that is low in power or is having some other type of performance issue may be skipped in the order.

In some example embodiments, the smartwatch, such as smartwatch 199A-B, may be configured to handle data connection losses, alerts, power outages, power saving modes, and missed alerts differently based on the role of the wearer of the smartwatch.

In some example embodiments, there may be a default configuration, so a certain device is always alerted, such as smartwatch 199A. If the alert is not acknowledged after a certain time, the alert is resent to another device such as device 112 or another remote user, such as the wearer of smartwatch 119B. Moreover, a certain phone may be assigned as the master to coordinate the scheme above.

In some example embodiments, there may be provided a way to let a user know if a smartwatch 199A and/or a device 112 coupled to the smartwatch 199A are not connected. For example, the link between watch and receiver/smartphone may be monitored. Alternatively or additionally, a CGM application on the smartwatch or smartphone may be monitored. In some example embodiments, a schedule may be configured on the devices. The device may provide for sleep time, wake up times, and the sending of keep alive (for example, phone tells watch to wake up periodically). In some example embodiments, the smartwatch may provide health message to smartphone 112 regarding power link status and/or the like.

In some example embodiments, the smartwatch 199A may have limited functionality when compared to a smartphone or tablet based receiver 112-113.

In some example embodiments, there may be provided actionable notifications. For example, if a certain alert is received at a smartwatch, the smartwatch may have pre-generated and pre-populated actionable notifications that prompt a user/wearer to act, such as calling a host-patient, calling for emergency help, sending a text (for example, eat an orange, call me or a doctor, etc.), and/or the like. Text could be prepopulated with a text statement or questions directed to the host. For non-limiting example, FIG. 3B depicts an embodiment of actionable notifications that can be performed by the user.

Figure 7:
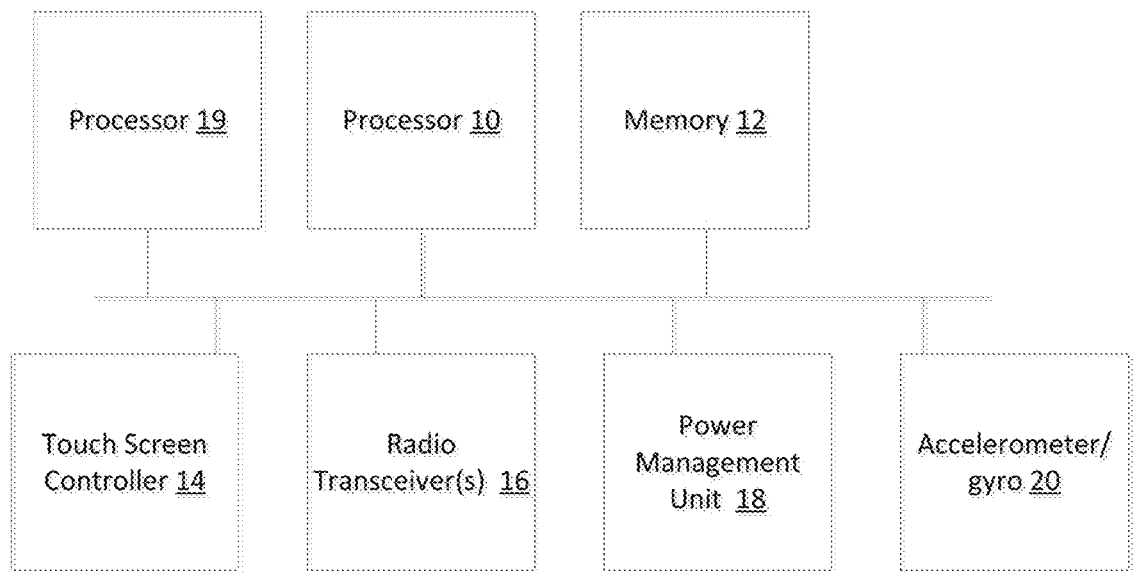
FIG. 7 depicts a block diagram of a smartwatch, in accordance with some example embodiments.

FIG. 7 depicts an example block diagram of an apparatus 700, such as smartwatch 199A-B, in accordance with some example embodiments. The apparatus may be implemented as a smartwatch as noted, but the apparatus may comprise other types of user equipment as well.

The apparatus of FIG. 7 may include at least one processor 10. The processor 10 may, for example, be embodied in a variety of ways including circuitry having one or more of the following: at least one processing core, one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits (for example, an application specific integrated circuit (ASIC), a field programmable gate array (FPGA), and/or the like), or some combination thereof. The apparatus 700 may include at least one memory 12, such as volatile memory and/or non-volatile memory. The apparatus 700 may also include touchscreen controller circuitry 14 for controlling the touchscreen display 19, detecting gestures including touches at the display 19, and/or the like. The apparatus 700 may include at least one radio transceiver 16. The radio transceiver may be configured to transmit and/or receive in accordance with one or more radio air interface standards, communication protocols, modulation types, access types, and/or the like. For example, the radio transceiver(s) 16 be configured to provide one or more transceiver configured to operate in accordance with WiFi, 2G, 2.5G, 3G, 4G, 5G, Long Term Evolution (LTE), LTE Advanced, LTE-Direct, LTE-Unlicensed, infrared (IR), Bluetooth, wireless universal serial bus, Bluetooth Low Energy, ZigBee, ANT, Near Field Communication (NFC), and/or the like. The apparatus 700 may also include a power management unit to manage battery use and charging of batteries powering the smartwatch. The apparatus 700 may also include an accelerometer and/or gyro. The apparatus 700 may also include other user interface elements including an earphone or speaker, a ringer, a microphone, a display, a user input interface, a camera, and/or the like, all of which may be coupled to the processor 20.

Various implementations of the subject matter described herein may be realized in digital electronic circuitry, integrated circuitry, specially designed ASICs (application specific integrated circuits), computer hardware, firmware, software, and/or combinations thereof. The circuitry may be affixed to a printed circuit board (PCB), or the like, and may take a variety of forms, as noted. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a machine-readable medium that receives machine instructions. The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer readable medium" or "tangible memory" are intended to encompass types of storage devices that do not necessarily store information permanently, including for example, random access memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, audible feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

Although a few variations have been described in detail above, other modifications are possible. For example, while the descriptions of specific implementations of the current subject matter discuss analytic applications, the current subject matter is applicable to other types of software and data services access as well. Moreover, although the above description refers to specific products, other products may be used as well. In addition, the logic flows depicted in the accompanying figures and described herein do not require the particular order shown, or sequential order, to achieve desirable results. Other implementations may be within the scope of the following claims.

For ease of explanation and illustration, in some instances the detailed description describes exemplary systems and methods in terms of a continuous glucose monitoring environment; however it should be understood that the scope of the invention is not limited to that particular environment, and that one skilled in the art will appreciate that the systems and methods described herein can be embodied in various forms. Accordingly any structural and/or functional details disclosed herein are not to be interpreted as limiting the systems and methods, but rather are provided as attributes of a representative embodiment and/or arrangement for teaching one skilled in the art one or more ways to implement the systems and methods, which may be advantageous in other contexts.

For example, and without limitation, described monitoring systems and methods may include sensors that measure the concentration of one or more analytes (for instance glucose, lactate, potassium, pH, cholesterol, isoprene, and/or hemoglobin) and/or other blood or bodily fluid constituents of or relevant to a host and/or another party.

By way of example, and without limitation, monitoring system and method embodiments described herein may include finger-stick blood sampling, blood analyte test strips, non-invasive sensors, wearable monitors (e.g. smart bracelets, smart watches, smart rings, smart necklaces or pendants, workout monitors, fitness monitors, health and/or medical monitors, clip-on monitors, and the like), adhesive sensors, smart textiles and/or clothing incorporating sensors, shoe inserts and/or insoles that include sensors, transdermal (i.e. transcutaneous) sensors, and/or swallowed, inhaled or implantable sensors.

In some embodiments, and without limitation, monitoring systems and methods may comprise other sensors instead of or in additional to the sensors described herein, such as inertial measurement units including accelerometers, gyroscopes, magnetometers and/or barometers; motion, altitude, position, and/or location sensors; biometric sensors; optical sensors including for instance optical heart rate monitors, photoplethysmogram (PPG)/pulse oximeters, fluorescence monitors, and cameras; wearable electrodes; electrocardiogram (EKG or ECG), electroencephalography (EEG), and/or electromyography (EMG) sensors; chemical sensors; flexible sensors for instance for measuring stretch, displacement, pressure, weight, or impact; galvanometric sensors, capacitive sensors, electric field sensors, temperature/thermal sensors, microphones, vibration sensors, ultrasound sensors, piezoelectric/piezoresistive sensors, and/or transducers for measuring information of or relevant to a host and/or another party.

Exemplary Apparatus, Methods, and Media

Method 1. A method comprising: receiving, at a smartwatch, an alert representative of a glucose state of a host-patient coupled to a glucose sensor; detecting, at the smartwatch, a predetermined action indicative of a request to generate a glance view providing an indication of the glucose state of the host-patient; and presenting, at the smartwatch and in response to the detecting, the glance view providing the indication of the glucose state of the host-patient.

Method 2. The method of Method 1, wherein the alert is received via a low power radio access transceiver at the smartwatch.

Method 3. The method of Method 2, wherein the low power radio access transceiver is configured in accordance with at least one of Bluetooth, Bluetooth Low Energy, or NFC.

Method 4. The method of any one of Methods 2-3, wherein the alert is received from a receiver wirelessly coupled to the glucose sensor via transmitter sensor electronics.

Method 5. The method of Method 4, wherein the receiver comprises at least one of a smartphone and/or a tablet.

Method 6. The method of any one of Methods 4-5, wherein the receiver includes a continuous blood glucose application configured to interact with the smartwatch.

Method 7. The method of any one of Methods 1-6, wherein the alert is received from a remote server.

Method 8. The method of any one of Methods 1-7, wherein the detecting of the predetermined action triggers the smartwatch to replace a home screen and/or a default user interface view with the glance view.

Method 9. The method of any one of Methods 1-8, further comprising: triggering, at the smartwatch and in response to the detecting, a feedback comprising a haptic indicator, an audio indicator, and/or a visual indicator.

Method 10. The method of any one of Methods 1-9, wherein the predetermined action comprises a selection of a certain icon displayed on the smartwatch.

Method 11. The method of any one of Methods 1-10, wherein the predetermined action comprises a selection of a physical button.

Method 12. The method of any one of Methods 1-11, wherein the predetermined action comprises a detection of a certain wrist movement.

Method 13. The method of any one of Methods 1-12, wherein the predetermined action comprises a detection of a certain eye movement of a wearer of the smartwatch.

Method 14. The method of any one of Methods 1-13, further comprising: detecting a swipe pattern; mapping the detected swipe pattern to at least one of a plurality of glance views, each of which is mapped to a different swipe pattern; and presenting, based on the detected swipe pattern, the at least one glance view.

Method 15. The method of any one of Methods 1-14, further comprising: mapping the glucose state to at least one of a plurality of glance views, each of which is mapped to a different glucose state; and presenting, based on the glucose state, the at least one glance view.

Method 16. The method of any one of Methods 1-15, further comprising: determining a role of a wearer of the smartwatch; mapping the role of the wearer to at least one of a plurality of glance views, each of which is mapped to a different role; and presenting, based on the determined role, the at least one glance view.

Method 17. The method of any one of Methods 1-16, further comprising: presenting, based on what the smartwatch is directly coupled to, the glance view.

Method 18. The method of any one of Methods 1-17, wherein the glance view provides, in a single user interface view, a graphical indication of the glucose state including a rate of change of the glucose state.

Method 19. The method of Method 18, wherein the rate of change is represented by a quantity of arrows presented via the glance view, and wherein the glucose glance view further includes a current glucose value of the host-patient.

Method 20. The method of any one of Methods 1-10, further comprising: generating a dashboard including a plurality of icons corresponding to a plurality of host-patients, each of which having a corresponding glucose state.

Method 21. The method of Method 20, further comprising: selecting at least one of the plurality of icons in order to obtain additional information regarding the corresponding glucose state.

Method 22. The method of any one of Methods 20-21, further comprising: varying, based on a quantity of the plurality of icons, a size of the plurality of icons.

Method 23. The method of any one of Methods 20-22, further comprising: varying, based on a severity of the corresponding glucose state, an order of presentation for the plurality of icons.

Method 24. The method of any one of Methods 1-23, further comprising: handing off the glance view displayed at the smartwatch to another device to enable presentation of the glance view at the other device.

Method 25. The method of any one of Methods 1-25, further comprising: presenting a notification bar in the glance view in response to the alert; and detecting a user input to view the notification bar.

Method 26. The method of Method 25, wherein the user input is a finger swipe or a manipulation of a physical button.

Method 27. The method of any one of Methods 25-26, wherein the notification bar includes at least one actionable selection.

Method 28. The method of any one of Methods 25-27, wherein the actionable selection displays a map, displays a glucose trend chart, acknowledges the alert, or dismisses the alert.

Method 29. A method comprising: determining a quantity of followers being monitored via a dashboard view presented at a display of the smartwatch, the dashboard view including a plurality of icons corresponding to a plurality of host-patients, each of which having a corresponding glucose state; generating a display including the plurality of icons sized according to the determined quantity of followers; receiving a selection of a sized icon from among the plurality of icons; and displaying additional information regarding the corresponding glucose state of the host-patient corresponding to the selected, sized icon.

Method 30. The method of Method 29, wherein an identity of each of the plurality of host-patients is anonymized.

Method 31. The method of any one of Methods 29-30, further comprising detecting, at the smartwatch, a predetermined action indicative of a request to generate a glance view providing an indication of the glucose state of the host-patient.

Method 32. The method of Method 31, further comprising presenting, at the smartwatch and in response to the detecting, the glance view providing the indication of the glucose state of the host-patient.

Method 33. The method of Method 32, wherein the alert is received via a low power radio access transceiver at the smartwatch.

Method 34. The method of Method 33, wherein the low power radio access transceiver is configured in accordance with at least one of Bluetooth, Bluetooth Low Energy, or NFC.

Method 35. The method of any one of Methods 33-34, wherein the alert is received from a receiver wirelessly coupled to the glucose sensor via transmitter sensor electronics.

Method 36. The method of Method 35, wherein the receiver comprises at least one of a smartphone and/or a tablet.

Method 37. The method of any one of Methods 35-36, wherein the receiver includes a continuous blood glucose application configured to interact with the smartwatch.

Method 38 The method of Method 32, wherein the alert is received from a remote server.

Method 39. The method of any one of Methods 32-38, wherein the detecting of the predetermined action triggers the smartwatch to replace a home screen and/or a default user interface view with the glance view.

Method 40. The method of any one of Methods 32-39, further comprising: triggering, at the smartwatch and in response to the detecting, a feedback comprising a haptic indicator, an audio indicator, and/or a visual indicator.

Method 41. The method of any one of Methods 32-40, wherein the predetermined action comprises a selection of a physical button.

Method 42. The method of any one of Methods 32-41, wherein the predetermined action comprises a detection of a certain wrist movement.

Method 43. The method of any one of Methods 32-42, wherein the predetermined action comprises a detection of a certain eye movement of a wearer of the smartwatch.

Method 44. The method of any one of Methods 32-43, further comprising: detecting a swipe pattern; mapping the detected swipe pattern to at least one of a plurality of glance views, each of which is mapped to a different swipe pattern; and presenting, based on the detected swipe pattern, the at least one glance view.

Method 45. The method of any one of Methods 32-44 further comprising: mapping the glucose state to at least one of a plurality of glance views, each of which is mapped to a different glucose state; and presenting, based on the glucose state, the at least one glance view.

Method 46. The method of any one of Methods 32-45, further comprising: determining a role of a wearer of the smartwatch; mapping the role of the wearer to at least one of a plurality of glance views, each of which is mapped to a different role; and presenting, based on the determined role, the at least one glance view.

Method 47. The method of any one of Methods 32-46, further comprising: presenting, based on what the smartwatch is directly coupled to, the glance view.

Method 48. The method of any one of Methods 32-47, wherein the glance view provides, in a single user interface view, a graphical indication of the glucose state including a rate of change of the glucose state.

Method 49. The method of Method 48, wherein the rate of change is represented by a quantity of arrows presented via the glance view, and wherein the glucose glance view further includes a current glucose value of the host-patient.

Method 50. The method of any one of Methods 32-49, further comprising varying, based on a quantity of the plurality of icons, a size of the plurality of icons.

Method 51. The method of any one of Methods 32-50, further comprising: varying, based on a severity of the corresponding glucose state, an order of presentation for the plurality of icons.

Method 52. The method of any one of Methods 32-51, further comprising: handing off the glance view displayed at the smartwatch to another device to enable presentation of the glance view at the other device.

Method 53. A method comprising: receiving, at a smartwatch, an alert representative of a glucose state of a host-patient coupled to a glucose sensor; presenting, at the smartwatch, a user interface view representative of the glucose state; receiving a request to allow a handoff of the presented user interface view to another device; and presenting, at the other device and in response to the handoff, the user interface view.

Method 54. The method of Method 53, wherein the handoff is enabled via a remote server.

Apparatus 55. An apparatus comprising: at least one processor including at least one memory including program code which when executed by the at least one processor causes operations comprising: receiving, at the apparatus, an alert representative of a glucose state of a host-patient coupled to a glucose sensor; detecting, at the apparatus, a predetermined action indicative of a request to generate a glance view providing an indication of the glucose state of the host-patient; and presenting, at the apparatus and in response to the detecting, the glance view providing the indication of the glucose state of the host-patient.

Apparatus 56. The apparatus of Apparatus 55, wherein the apparatus comprises a smartwatch.

Apparatus 57. The apparatus of Apparatus 56, wherein the alert is received via a low power radio access transceiver at the smartwatch.

Apparatus 58. The apparatus of Apparatus 57, wherein the low power radio access transceiver is configured in accordance with at least one of Bluetooth, Bluetooth Low Energy, or NFC.

Apparatus 59. The apparatus of any one of Apparatuses 57-58, wherein the alert is received from a receiver wirelessly coupled to the glucose sensor via transmitter sensor electronics.

Apparatus 60. The apparatus of Apparatus 59, wherein the receiver comprises at least one of a smartphone and/or a tablet.

Apparatus 61. The apparatus of any one of Apparatuses 59-60, wherein the receiver includes a continuous blood glucose application configured to interact with the smartwatch.

Apparatus 62. The apparatus of any one of Apparatuses 55-61, wherein the alert is received from a remote server.

Apparatus 63. The apparatus of any one of Apparatuses 56-62, wherein the detecting of the predetermined action triggers the smartwatch to replace a home screen and/or a default user interface view with the glance view.

Apparatus 64. The apparatus of any one of Apparatuses 56-63, further comprising: triggering, at the smartwatch and in response to the detecting, a feedback comprising a haptic indicator, an audio indicator, and/or a visual indicator.

Apparatus 65. The apparatus of any one of Apparatuses 56-64, wherein the predetermined action comprises a selection of a certain icon displayed on the smartwatch.

Apparatus 66. The apparatus of any one of Apparatuses 56-65, wherein the predetermined action comprises a selection of a physical button.

Apparatus 67. The apparatus of any one of Apparatuses 56-66, wherein the predetermined action comprises a detection of a certain wrist movement.

Apparatus 68. The apparatus of any one of Apparatuses 56-67, wherein the predetermined action comprises a detection of a certain eye movement of a wearer of the smartwatch.

Apparatus 69. The apparatus of any one of Apparatuses 56-68, further comprising: detecting a swipe pattern; mapping the detected swipe pattern to at least one of a plurality of glance views, each of which is mapped to a different swipe pattern; and presenting, based on the detected swipe pattern, the at least one glance view.

Apparatus 70. The apparatus of any one of Apparatuses 56-70, further comprising: mapping the glucose state to at least one of a plurality of glance views, each of which is mapped to a different glucose state; and presenting, based on the glucose state, the at least one glance view.

Apparatus 71. The apparatus of any one of Apparatuses 56-70, further comprising: determining a role of a wearer of the smartwatch; mapping the role of the wearer to at least one of a plurality of glance views, each of which is mapped to a different role; and presenting, based on the determined role, the at least one glance view.

Apparatus 72. The apparatus of any one of Apparatuses 56-71, further comprising: presenting, based on what the smartwatch is directly coupled to, the glance view.

Apparatus 73. The apparatus of any one of Apparatus 56-73, wherein the glance view provides, in a single user interface view, a graphical indication of the glucose state including a rate of change of the glucose state.

Apparatus 74. The apparatus of Apparatus 73, wherein the rate of change is represented by a quantity of arrows presented via the glance view, and wherein the glucose glance view further includes a current glucose value of the host-patient.

Apparatus 75. The apparatus of any one of Apparatus 56-74, further comprising: generating a dashboard including a plurality of icons corresponding to a plurality of host-patients, each of which having a corresponding glucose state.

Apparatus 76. The apparatus of any one of Apparatuses 56-75, further comprising: selecting at least one of the plurality of icons in order to obtain additional information regarding the corresponding glucose state.

Apparatus 77. The apparatus of any one of Apparatuses 56-76, further comprising: varying, based on a quantity of the plurality of icons, a size of the plurality of icons.

Apparatus 78. The apparatus of any one of Apparatuses 56-77, further comprising: varying, based on a severity of the corresponding glucose state, an order of presentation for the plurality of icons.

Apparatus 79. The apparatus of any one of Apparatuses 56-78, further comprising: handing off the glance view displayed at the smartwatch to another device to enable presentation of the glance view at the other device.

Apparatus 80. An apparatus comprising: at least one processor including at least one memory including program code which when executed by the at least one processor causes operations comprising: determining a quantity of followers being monitored via a dashboard view presented at a display of the smartwatch, the dashboard view including a plurality of icons corresponding to a plurality of host-patients, each of which having a corresponding glucose state; generating a display including the plurality of icons sized according to the determined quantity of followers; receiving a selection of a sized icon from among the plurality of icons; and displaying additional information regarding the corresponding glucose state of the host-patient corresponding to the selected, sized icon.

Apparatus 81. The apparatus of Apparatus 80, wherein the apparatus comprises a smartwatch.

Apparatus 82. The apparatus of any one of Apparatuses 80-81, wherein an identity of each of the plurality of host-patients is anonymized.

Apparatus. 83. An apparatus comprising: at least one processor including at least one memory including program code which when executed by the at least one processor causes operations comprising: receiving, at the apparatus, an alert representative of a glucose state of a host-patient coupled to a glucose sensor; presenting, at the apparatus, a user interface view representative of the glucose state;

receiving a request to allow a handoff of the presented user interface view to another device; and presenting, at the other device and in response to the handoff, the user interface view.

Apparatus 84. The apparatus of Apparatus 83, wherein the apparatus comprises a smartwatch.

Apparatus 85. The apparatus of any one of Apparatuses 83-84, wherein the handoff is enabled via a remote server.

Non-transitory computer readable storage medium 86. A non-transitory computer readable storage medium storing instructions that, when executed by at least one programmable processor forming part of at least one computing system, cause the at least one programmable processor to perform operations comprising: receiving an alert representative of a glucose state of a host-patient coupled to a glucose sensor; detecting a predetermined action indicative of a request to generate a glance view providing an indication of the glucose state of the host-patient; and presenting, in response to the detecting, the glance view providing the indication of the glucose state of the host-patient.

Non-transitory computer readable storage medium 87. A non-transitory computer readable storage medium storing instructions that, when executed by at least one programmable processor forming part of at least one computing system, cause the at least one programmable processor to perform operations comprising: determining a quantity of followers being monitored via a dashboard view at a display of the apparatus, the dashboard view including a plurality of icons corresponding to a plurality of host-patients, each of which having a corresponding glucose state; generating a display with the plurality of icons sized according to the determined quantity of followers; receiving a selection of a sized icon from among the plurality of icons; and displaying additional information regarding the corresponding glucose state of the host-patient corresponding to the selected, sized icon host-patient.

Non-transitory computer readable storage medium 88. A non-transitory computer readable storage medium storing instructions that, when executed by at least one programmable processor forming part of at least one computing system, cause the at least one programmable processor to perform operations comprising: receiving an alert representative of a glucose state of a host-patient coupled to a glucose sensor; presenting a user interface view representative of the glucose state; receiving a request to allow a handoff of the presented user interface view to another device; and presenting, in response to the handoff, the user interface view at another device.

Any of the features of any of the above-referenced methods, apparatus, and non-transitory computer readable storage media is applicable to all aspects and embodiments identified herein. Moreover, any of the features of the above-referenced methods, apparatus, and non-transitory computer readable storage media is independently combinable, partly or wholly with any other of the above-referenced methods, apparatus, and non-transitory computer readable storage media, in whole or in part. Further, any of the features of any of the above-referenced methods, apparatus, and non-transitory computer readable storage media may be made optional to other aspects or embodiments. Any aspect or embodiment of a method can be performed by a system or apparatus of another aspect or embodiment, any aspect or embodiment of a system or apparatus can be configured to perform a method of another aspect or embodiment, and any aspect or embodiment of a media can be configured to perform a method of another aspect or embodiment.

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method comprising:
    receiving, at a smartwatch, an alert representative of a glucose state of a host-patient coupled to a glucose sensor, the glucose state comprising a glucose value or glucose rate of change value meeting a first criteria;
    detecting, at the smartwatch, in response to the alert, a predetermined action indicative of a request to generate a glance view of glucose information associated with the alert;
    selecting, at the smartwatch, based on the glucose state represented by the alert, a smartwatch view from two or more smartwatch views associated with two or more different glucose states, wherein the two or more smartwatch views each provide a different set of glucose information elements;
    presenting, at the smartwatch, in response to the detecting, the selected smartwatch view as the glance view; and
    handing off, by the smartwatch, the glance view to another device to enable presentation of content related to the glance view at the other device, the handing off comprising indicating, to the other device, at least one of: the selected and presented smartwatch view, or a user interface view to present at the other device.

2. The method of claim 1, wherein the alert is received via a low power radio access transceiver at the smartwatch.

3. The method of claim 2, wherein the low power radio access transceiver is configured in accordance with at least one of Bluetooth, Bluetooth Low Energy, or NFC.

4. The method of claim 2, wherein the alert is received from a receiver wirelessly coupled to the glucose sensor via transmitter sensor electronics.

5. The method of claim 4, wherein the receiver comprises at least one of a smartphone or a tablet.

6. The method of claim 4, wherein the receiver includes a continuous blood glucose application configured to interact with the smartwatch.

7. The method of claim 1, wherein the alert is received from a remote server.

8. The method of claim 1, wherein the detecting of the predetermined action triggers the smartwatch to replace a home screen and/or a default user interface view with the glance view.

9. The method of claim 1, further comprising:
    triggering, at the smartwatch and in response to the detecting, a feedback comprising a haptic indicator, an audio indicator, and/or a visual indicator.

10. The method of claim 1, wherein the predetermined action a selection of a physical button.

11. The method of claim 1, wherein the predetermined action comprises at least one of a detection of a certain wrist movement or a detection of a certain eye movement of a wearer of the smartwatch.

12. The method of claim 1, wherein the indicating comprises sending, to the other device, an index associated with the at least one of the selected and presented smartwatch view or the user interface view to present at the other device.

13. The method of claim 1, further comprising:
   detecting a swipe pattern;
   mapping the detected swipe pattern to at least one of a plurality of glance views, each of which is mapped to a different swipe pattern; and
   presenting, based on the detected swipe pattern, the at least one glance view.

14. The method of claim 1, further comprising:
   mapping the glucose state to at least one of a plurality of glance views, each of which is mapped to a different glucose state; and
   presenting, based on the glucose state, the at least one glance view.

15. The method of claim 1, further comprising:
   determining a role of a wearer of the smartwatch;
   mapping the role of the wearer to at least one of a plurality of glance views, each of which is mapped to a different role; and
   wherein the glance view comprises the at least one glance view.

16. The method of claim 1, wherein the glance view provides, in a single user interface view, a graphical indication of the glucose state including a rate of change of the glucose state.

17. The method of claim 1, further comprising:
   generating a dashboard including a plurality of icons corresponding to a plurality of host-patients, each of which having a corresponding glucose state.

18. The method of claim 1, further comprising:
   presenting a notification bar in the glance view in response to the alert; and
   detecting a user input to view the notification bar.

19. The method of claim 18, wherein the notification bar includes at least one actionable selection that displays a map, displays a glucose trend chart, acknowledges the alert, or dismisses the alert.

20. The method of claim 1, further comprising:
   receiving, at the smartwatch, a second alert representative of a second glucose state of the host-patient, the second glucose state comprising a second glucose value or second glucose rate of change value meeting a second criteria;
   detecting, at the smartwatch, in response to the second alert, a second predetermined action indicative of a request to generate a second glance view of glucose information associated with the second alert;
   selecting, at the smartwatch, based on the second glucose state represented by the second alert, a second smartwatch view from the two or more smartwatch views, wherein the selected second smartwatch view is different from the selected smartwatch view; and
   presenting, at the smartwatch, in response to the detecting the second predetermined action, the selected second smartwatch view as the second glance view.

21. The method of claim 1, further comprising receiving, at the smartwatch, a selection of the glance view, wherein the smartwatch triggers the handing off in response to the selection.

22. The method of claim 1, wherein the indicating comprises sending, by the smartwatch, a message to the other device, the message identifying the selected and presented smartwatch view.

23. The method of claim 1, wherein the indicating comprises sending, by the smartwatch, a message to the other device, the message identifying the user interface view to present at the other device.

24. The method of claim 23, further comprising presenting, at the other device, in response to the handing off, the user interface view.

25. The method of claim 24, wherein the other device has a larger display area than the smartwatch and the user interface view is more detailed than the selected and presented smartwatch view.

26. A non-transitory computer readable storage medium storing instructions that, when executed by at least one programmable processor forming part of at least one computing system, cause the at least one programmable processor to perform operations comprising:
   receiving an alert representative of a glucose state of a host-patient coupled to a glucose sensor, the glucose state comprising a glucose value or glucose rate of change value meeting a first criteria;
   detecting, in response to the alert, a predetermined action indicative of a request to generate a glance view of glucose information associated with the alert;
   selecting, based on the glucose state represented by the alert, a smartwatch view from two or more smartwatch views associated with two or more different glucose states, wherein the two or more smartwatch views each provide a different set of glucose information elements;
   presenting, in response to the detecting, the selected smartwatch view as the glance view; and
   handing off the glance view to another device to enable presentation of content related to the glance view at the other device, the handing off comprising indicating, to the other device, at least one of:
      the selected and presented smartwatch view, or
      a user interface view to present at the other device.

27. The non-transitory computer readable storage medium of claim 26, wherein the alert is received via a low power radio access transceiver at a smartwatch.

28. The non-transitory computer readable storage medium of claim 26, wherein the alert is received from a receiver wirelessly coupled to the glucose sensor via transmitter sensor electronics.

29. The non-transitory computer readable storage medium of claim 28 wherein the receiver comprises at least one of a smartphone or a tablet.

30. The non-transitory computer readable storage medium of claim 28, wherein the receiver includes a continuous blood glucose application configured to interact with a smartwatch.

* * * * *